US011096583B2

(12) United States Patent
Emerson et al.

(10) Patent No.: US 11,096,583 B2
(45) Date of Patent: Aug. 24, 2021

(54) METHODS, SYSTEMS, AND COMPUTER READABLE MEDIA FOR UTILIZING FUNCTIONAL CONNECTIVITY BRAIN IMAGING FOR DIAGNOSIS OF A NEUROBEHAVIORAL DISORDER

(71) Applicants: The University of North Carolina at Chapel Hill, Chapel Hill, NC (US); Washington University, St. Louis, MO (US)

(72) Inventors: Robert Wayne Emerson, Durham, NC (US); Joseph Piven, Pittsboro, NC (US); Bradley Schlaggar, Towson, MD (US); John Pruett, Jr., Richmond Heights, MO (US)

(73) Assignees: The University of North Carolina at Chapel Hill, Chapel Hill, NC (US); Washington University, St. Louis, MO (US)

(*) Notice: Subject to any disclaimer, the term of this patent is extended or adjusted under 35 U.S.C. 154(b) by 0 days.

(21) Appl. No.: 16/235,402

(22) Filed: Dec. 28, 2018

(65) Prior Publication Data

US 2019/0133446 A1 May 9, 2019

Related U.S. Application Data

(63) Continuation of application No. PCT/US2017/040032, filed on Jun. 29, 2017.
(Continued)

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/168* (2013.01); *A61B 5/4064* (2013.01);
(Continued)

(58) Field of Classification Search
CPC ..... A61B 5/0042; A61B 5/168; A61B 5/4064; A61B 5/7264; A61B 5/055; A61B 5/0476;
(Continued)

(56) References Cited

U.S. PATENT DOCUMENTS 7,751,602 B2 7/2010 Collins et al.
7,899,255 B2 3/2011 Lindgren et al.
(Continued)

FOREIGN PATENT DOCUMENTS

CA 2 565 646 A1 4/2008
CA 2 752 370 A1 3/2013

OTHER PUBLICATIONS

Sacrey, Lori-Ann R. et al. Can Parents' Concerns Predict Autism Spectrum Disorder [online]. Journal of the American Academy of Child & Adolescent Psychiatry, Jun. 2015 [retrieved on Jun. 28, 2019], vol. 54, No. 6, pp. 470-478. Retrieved from the Internet: [URL: see office action] [DOI: see office action].*
(Continued)

*Primary Examiner* — Carolyn A Pehlke
*Assistant Examiner* — Victoria Fang
(74) *Attorney, Agent, or Firm* — Jenkins, Wilson, Taylor & Hunt, P.A.

(57) ABSTRACT

Methods, systems, and computer readable media for utilizing functional connectivity brain imaging for diagnosis of a neurobehavioral disorder are disclosed. One method for utilizing functional connectivity brain imaging for diagnosis of a neurobehavioral disorder includes receiving brain imag-
(Continued)

ing data for a human subject of a first age, wherein the brain imaging data includes functional connectivity magnetic resonance imaging (fcMRI) data, and predicting, using at least one functional connection between brain locations in the fcMRI data, a neurobehavioral disorder diagnosis for the subject at a second age greater than the first age.

13 Claims, 14 Drawing Sheets

Related U.S. Application Data

(60) Provisional application No. 62/356,485, filed on Jun. 29, 2016.

(51) Int. Cl.
   *G01R 33/48*   (2006.01)
   *G06T 7/00*    (2017.01)
   *G06N 20/10*   (2019.01)
   *A61B 5/16*    (2006.01)
   *A61B 5/369*   (2021.01)

(52) U.S. Cl.
   CPC ........ *A61B 5/7264* (2013.01); *G01R 33/4806* (2013.01); *G06T 7/0012* (2013.01); *A61B 5/167* (2013.01); *A61B 5/369* (2021.01); *A61B 2576/026* (2013.01); *G01R 33/4808* (2013.01); *G06N 20/10* (2019.01); *G06T 2207/10088* (2013.01); *G06T 2207/30016* (2013.01)

(58) Field of Classification Search
   CPC . A61B 5/167; A61B 2576/026; G06T 7/0012; G06T 2207/30016; G06T 2207/10088; G01R 33/4806; G01R 33/4808; G06N 20/00; G06N 20/10
   USPC ........................................................ 600/410
   See application file for complete search history.

(56) References Cited

U.S. PATENT DOCUMENTS

| | | | |
|---|---|---|---|
| 8,699,776 B2 | 4/2014 | Duschesne | |
| 2011/0218253 A1* | 9/2011 | Lange ..................... | A61K 45/00 514/789 |
| 2013/0116540 A1* | 5/2013 | Li .......................... | A61B 5/055 600/410 |
| 2013/0231552 A1* | 9/2013 | Grady .................... | A61B 5/055 600/410 |
| 2014/0222738 A1 | 8/2014 | Joyce et al. | |
| 2014/0226882 A1 | 8/2014 | Collins et al. | |
| 2015/0080703 A1* | 3/2015 | Reiman ................ | A61B 5/4848 600/409 |
| 2015/0272461 A1* | 10/2015 | Morimoto .......... | A61B 5/04012 600/410 |
| 2015/0313913 A1* | 11/2015 | Catterall ............ | A61K 31/4355 514/169 |
| 2019/0148021 A1 | 5/2019 | Styner et al. | |
| 2019/0209097 A1* | 7/2019 | Martien ............... | A61B 5/4076 |
| 2019/0287247 A1 | 9/2019 | Duchesne et al. | |

OTHER PUBLICATIONS

Pruett, John R., Jr. et al. Accurate age classification of 6 and 12 month-old infants based on resting-state functional connectivity magnetic resonance imaging data [online]. Developmental Cognitive Neuroscience, Apr. 2015 [retrieved on Jun. 28, 2019], vol. 12, pp. 123-133. Retrieved from the Internet: see action.*
Autism—Brain Regions and their Dysfunctions [online]. Brain Maps, Aug. 5, 2009 [retrieved on Jul. 1, 2019], pp. 1-4. Retrieved from the Internet: <URL: https://web.archive.org/web/20090805233139/ http://www.brain-maps.com/autism. html>.*
Vergun et al., "Characterizing functional connectivity differences in aging adults using machine learning on resting state fMRI data," Frontiers in Computational Neuroscience, vol. 7, Article 38, pp. 1-20 (Apr. 2013).*
Sladsky et al., "Slice-timing effects and their correction in functional MRI," Neuroimage, vol. 58, pp. 558-594 (2011).*
Elsabbagh, Mayada, et al. Infant Neural Sensitivity to Dynamic Eye Gaze Is Associated with Later Emerging Autism [online], Current Biology, Feb. 21, 2012 [retrieved on Dec. 16, 2019], vol. 22, No. 4, pp. 338-342. Retrieved from the Internet: <URL/DOI: see Office action>. (Year: 2012).*
Wolff et al. Differences in White Matter Fiber Tract Development Present From 6 to 24 Months in Infants With Autism. Am. J. Psychiatry, Jun. 2012 [retrieved on Jul. 15, 2020], vol. 169, pp. 589-600. Retrieved from the Internet: <URL/DOI: see Office action>. (Year: 2012).*
Pereira et al. Machine learning classifiers and fMRI: a tutorial overview. NeuroImage, Mar. 2009 [available online Nov. 21, 2008, retrieved on Jul. 15, 2020], vol. 45, No. 1, p. S199-S209. Retrieved from the Internet: <URL/DOI: see Office action>. (Year: 2009).*
Kuhn, Max, and Kjell Johnson. Applied Predictive Modeling [online]. Springer, 2013 [retrieved on Nov. 5, 2020], Chapter 19: An Introduction to Feature Selection, pp. 487-519. Retrieved from the Internet: <URL: https://link.springer.com/book/10.1007/978-1-4614-6849-3>. (Year: 2013).*
Jin, Yan et al. Identification of Infants at High-Risk for Autism Spectrum Disorder Using Multiparameter Multiscale White Matter Connectivity Networks [online]. Human Brain Mapping, Sep. 14, 2015 [retrieved on Nov. 5, 2020], vol. 36, No. 12, pp. 4880-4896. Retrieved from the Internet. (Year: 2015).*
Neilson, Jared A., et al. Multisite functional connectivity MRI classification of autism: ABIDE results [online]. Front. Hum. Neurosci., Sep. 25, 2013 [retrieved on Mar. 26, 2021], pp. 1-12. Retrieved from the Internet: <URL: https://www.frontiersin.org/ articles/10.3389/fnhum.2013.00599/full>.*
[Item U continued] <DOI: 10.3389/fnhum.2013.00599>. (Year: 2013).*
Restriction Requirement for U.S. Appl. No. 16/235,379 (dated May 2, 2019).
Notification of Transmittal of the International Search Report and the Written Opinion of the International Searching Authority, or the Declaration for International Application No. PCT/US2017/040032 (dated Sep. 7, 2017).
Jones et al., "Attention to eyes is present but in decline in 2-6-month-old infants later diagnosed with autism," Nature, vol. 504, pp. 427-431 (Nov. 6, 2013).
Vergun et al., "Characterizing functional connectivity differences in aging adults using machine learning on resting state fMRI data," Frontiers in Computational Neuroscience, vol. 7, Article 38, pp. 1 (Apr. 2013).
Sladky et al., "Slice-timing effects and their correction in functional MRI," NeuroImage, vol. 58, pp. 588-594 (2011).
"DSM-5," Wikipedia, https://en.wikipedia.org/wiki/DSM-5, pp. 1-17 (Mar. 5, 2019).
"Diagnostic and Statistical Manual of Mental Disorders," Wikipedia, https://en.wikipedia.org/wiki/Diagnostic_and_Statistical_Manual_of_Mental_Disorders, pp. 1-19 (Mar. 2, 2019).
"Prevalence and Characteristics of Autism Spectrum Disorder Among Children Aged 8 Years—Autism and Developmental Disabilities Monitoring Network, 11 Sites, United States, 2012," Centers for Disease Control and Prevention, Morbidity and Mortality Weekly Report, Surveillance Summaries, vol. 65, No. 13, https://www.cdc.gov/mmwr/volumes/65/ss/pdfs/ss6513a1-H.pdf, pp. 1-28 (Nov. 16, 2018).
Abu-Akel et al., "Mind the prevalence rate: overestimating the clinical utility of psychiatric diagnostic classifiers," Psychological Medicine, vol. 48, pp. 1-3 (2018).
Notification of Transmittal of the International Search Report and the Written Opinion of the International Searching Authority, or the Declaration for International Patent Application Serial No. PCT/US 2017/040041 (dated Jun. 29, 2017).

(56) References Cited

OTHER PUBLICATIONS

Greene et al., "Multivariate pattern classification of pediatric Tourette syndrome using functional connectivity MRI," Developmental Science, vol. 19, No. 4, pp. 581-598 (2016).
Lenz, "Deep learning for robotics," Cornell University, pp. 1-155 (Jan. 2016).
Rosenberg et al., "A neuromarker of sustained attention from whole-brain functional connectivity," Nat. Neurosci., vol. 19, No. 1, pp. 165-171 (Jan. 2016).
Cotney et al., "The autism-associated chromatin modifier CHD8 regulates other autism risk genes during human neurodevelopment," Nature Communications, pp. 1-11 (2015).
Estes et al., "Behavioral, cognitive, and adaptive development in infants with autism spectrum disorder in the first 2 years of life," Journal of Neurodevelopmental Disorders, vol. 7, No. 24, pp. 1-10 (2015).
Pruett et al., "Accurate age classification of 6 and 12 month-old infants based on resting-state functional connectivity magnetic resonance imaging data," Developmental Cognitive Neuroscience, vol. 12, pp. 123-133 (2015).
Finn et al., "Functional connectome fingerprinting: identifying individuals using patterns of brain connectivity," Nat. Neurosci., vol. 18, pp. 1-26 (Nov. 2015).
Li et al., "A Robust Deep Model for Improved Classification of AD/MCI Patients," IEEE J Biomed Health Inform, vol. 19, No. 5, pp. 1-19 (Sep. 2015).
Wolff et al., "Altered corpus callosum morphology associated with autism over the first 2 years of life," Brain, vol. 138, pp. 2046-2058 (May 3, 2015).
Gao et al., "Development of human brain cortical network architecture during infancy," Brain Struct. Funct., vol. 220, No. 2, pp. 1-25 (Mar. 2015).
Green et al., "Parent-mediated intervention versus no. intervention for infants at high risk of autism: a parallel, single-blind, randomised trial," Lancet. Psyc., vol. 2, pp. 133-140 (Feb. 2015).
Gabrieli et al., "Prediction as a Humanitarian and Pragmatic Contribution from Human Cognitive Neuroscience," Neuron, vol. 85, pp. 11-26 (Jan. 7, 2015).
Li et al., "A Robust Deep Learning for Improved Classification of AD/MCI Patients," Machine Learning in Medical Imaging (MLMI) Workshop, vol. 8679, pp. 240-247 (2014).
Pucilowska et al., "The 16p11.2 Deletion Mouse Model of Autism Exhibits Altered Cortical Progenitor Proliferation and Brain Cytoarchitecture Linked to the ERK MAPK Pathway," The Journal of Neuroscience, vol. 35, No. 7, pp. 3190-3200 (Feb. 18, 2015).
Charman, "Early identification and intervention in autism spectrum disorders: Some progress but not as much as we hoped," International Journal of Speech-Language Pathology, vol. 16, No. 1, pp. 15-18 (2014).
Rogers et al., "Autism treatment in the first year of life: a pilot study of infant start, a parent-implemented intervention for symptomatic infants," J. Autism. Dev. Disord., vol. 44, No. 12, pp. 1-25, (Dec. 2014).
Bernier et al., "Disruptive CHD8 mutations define a subtype of autism early in development," Cell, vol. 158, No. 2, pp. 1-27 (Jul. 17, 2014).
Buescher et al. "Costs of Autism Spectrum Disorders in the United Kingdom and the United States," JAMA Pediatr., vol. 168, pp. 721-728 (Jun. 9, 2014).
Chawarska et al., "18-Month Predictors of Later Outcomes in Younger Siblings of Children With Autism Spectrum Disorder: A Baby Siblings Research Consortium Study," J. Am. Acad. Child Adolesc Psychiatry, vol. 53, No. 12, pp. 1-18 (Dec. 2014).
Gan et al., "Deep self-taught learning for facial beauty prediction," Neurocomputing, vol. 144, pp. 295-303 (2014).
Li et al., "Mapping Longitudinal Hemispheric Structural Asymmetries of the Human Cerebral Cortex from Birth to 2 Years of Age," Cerebral Cortex, vol. 24, pp. 1289-1300 (2013).

Mirzaa et al., "Megalencephaly and Hemimegalencephaly: Breakthroughs in Molecular Etiology," American Journal of Medical Genetics Part C (Seminars in Medical Genetics), vol. 166C, pp. 156-172 (2014).
Ozonoff et al., "The broader autism phenotype in infancy: When does it emerge?," J Am Acad Child Adolesc Psychiatry, vol. 53, No. 4, pp. 1-19 (Apr. 2014).
Qureshi et al., "Opposing Brain Differences in 16p11.2 Deletion and Duplication Carriers," The Journal of Neuroscience, vol. 34, No. 34, pp. 11199-11211 (Aug. 20, 2014).
Sugathan et al., "CHD8 regulates neurodevelopmental pathways associated with autism spectrum disorder in neural progenitors," PNAS, pp. E4468-E4477 (Oct. 7, 2014).
Wang et al., "Multi-atlas segmentation of subcortical brain structures via the AutoSeg software pipeline," Frontiers in Neuroinformatics, vol. 8, No. 7, pp. 1-11 (Feb. 2014).
Webb et al., "The motivation for very early intervention for infants at high risk for autism spectrum disorders," Int. J. Speech. Lang. Pathol., vol. 16, pp. 1-11 (Feb. 2014).
Wolff et al., "Longitudinal Patterns of Repetitive Behavior in Toddlers with Autism," J Child Psychol Psychiatry, vol. 55, No. 8, pp. 1-17 (Aug. 2014).
Retico et al., "Neuroimaging-based methods for autism identification: a possible translational application?," Functional Neurology, vol. 29, No. 4, pp. 231-239 (2014).
Ciresan et al., "Mitosis Detection in Breast Cancer Histology Images with Deep Neural Networks," MICCAI, Nagoya, Japan, pp. 1-8 (2013).
Georgiades et al., "A Prospective Study of Autistic-Like Traits in Unaffected Siblings of Probands With Autism Spectrum Disorder," JAMA Psychiatry, vol. 70, No. 1, pp. 42-48 (2013).
Elison et al., "White Matter Microstructure and Atypical Visual Orienting in 7-Month-Olds at Risk for Autism," Am. J. Psychiatry, vol. 170, No. 8, pp. 1-18 (Aug. 1, 2013).
Uddin et al., "Salience Network-Based Classification and Prediction of Symptom Severity in Children with Autism," JAMA Psychiatry, vol. 70, pp. 869-879 (Jun. 2013).
Fair et al., "Distinct neural signatures detected for ADHD subtypes after controlling for micro-movements in resting state functional connectivity MRI data," Frontiers in Systems Neuroscience, vol. 6, Article 80, pp. 1-31 (Feb. 4, 2013).
Guthrie et al., "Early diagnosis of autism spectrum disorder: Stability and change in clinical diagnosis and symptom presentation," J Child Psychol Psychiatry, vol. 54, No. 5, pp. 1-18 (May 2013).
Castellanos et al., "Clinical applications of the functional connectome," Neuroimage, vol. 80, pp. 1-33 (Oct. 15, 2013).
Ecker et al., "Translational approaches to the biology of Autism: false dawn or a new era?," Molecular Psychiatry, vol. 18, pp. 435-442 (2013).
Kim et al., "Adaptive prior probability and spatial temporal intensity change estimation for segmentation of the one-year-old human brain," Journal of Neuroscience Methods, vol. 212, No. 1, pp. 1-27 (2013).
Landa et al., "Developmental Trajectories in Children With and Without Autism Spectrum Disorders: The First 3 Years," Child Dev., vol. 84, No. 2, pp. 1-21 (2013).
Messinger et al., "Beyond Autism: A Baby Siblings Research Consortium Study of High-Risk Children at Three Years of Age," J Am Child Adolesc Psychiatry, vol. 52, No. 3, pp. 1-17 (Mar. 2013).
Nonaka-Kinoshita et al., "Regulation of cerebral cortex size and folding by expansion of basal progenitors," The EMBO Journal, vol. 32, pp. 1817-1828 (2013).
Raznahan et al., "Compared to What? Early Brain Overgrowth in Autism and the Perils of Population Norms," Biol Psychiatry, vol. 74, pp. 563-575 (2013).
Shen et al., "Early brain enlargement and elevated extra-axial fluid in infants who develop autism spectrum disorder," Brain, vol. 136, pp. 2825-2835 (2013).
Suk et al., "Deep Learning-Based Feature Representation for AD/MCI Classification," Medical Image Computing and Computer Assisted Intervention (MICCAI), Lecture Notes in Computer Science, vol. 16, pp. 1-11 (2013).

(56) References Cited

OTHER PUBLICATIONS

Satterthwaite et al., "Heterogeneous Impact of Motion on Fundamental Patterns of Developmental Changes in Functional Connectivity During Youth," Neuroimage, vol. 83, pp. 1-27 (Dec. 2013).
Turner-Brown et al., "The First Year Inventory: A longitudinal follow-up of 12-month-olds to 3 years of age," Autism, vol. 17, No. 5, pp. 1-17 (Sep. 2013).
Fishbaugh et al., "A framework for longitudinal data analysis via shape regression," Proc SPIE, pp. 1-11 (Feb. 23, 2012).
Elsabbagh et al., "Infant Neural Sensitivity to Dynamic Eye Gaze is Associated with Later Emerging Autism," Current Biology, vol. 22, pp. 338-342 (Feb. 21, 2012).
Van Dijk et al., "The Influence of Head Motion on Intrinsic Functional Connectivity MRI," Neuroimage, vol. 59, No. 1, pp. 1-19 (Jan. 2, 2012).
Emerson et al., "Early math achievement and functional connectivity in the fronto-parietal network," Developmental Cognitive Neuroscience, vol. 2S, pp. S139-S151 (2012).
Hao et al., "Gated Boltzmann Machine in Texture Modeling," International Conference on Artificial Neural Networks and Machine Learning (ICANN), Lecture Notes in Computer Science, vol. 7553, pp. 1-8 (2012).
Hazlett et al., "Brain Volume Findings in Six Month Old Infants at High Familial Risk for Autism," Am J Psychiatry, vol. 169, No. 6, pp. 1-17 (Jun. 2012).
Huang et al., "Learning Hierarchical Representations for Face Verification with Convolutional Deep Belief Networks," IEEE Conference on Computer Vision and Pattern Recognition (CVPR), pp. 1-8 (2012).
Shin et al., "Stacked Autoencoders for Unsupervised Feature Learning and Multiple Organ Detection in a Pilot Study Using 4D Patient Data," IEEE Transactions on Pattern Analysis and Machine Intelligence, vol. 35, No. 8, pp. 1-14 (2012).
Shaw et al., "Development of Cortical Surface Area and Gyrification in Attention-Deficit/Hyperactivity Disorder," Biol Psychiatry, vol. 72, No. 3, pp. 191-197 (2012).
Wolff et al., "Differences in White Matter Fiber Tract Development Present From 6 to 24 Months in Infants With Autism," Am. J. Psychiatry, vol. 169, pp. 589-600 (2012).
Avants et al., "A Reproducible Evaluation of ANTs Similarity Metric Performance in Brain Image Registration," Neuroimage, vol. 54, no. 3, pp. 1-28 (Feb. 1, 2011).
Chawarska et al., "Early Generalized Overgrowth in Boys with Autism," Arch Gen Psychiatry, vol. 68, No. 10, pp. 1-23 (Oct. 2011).
Fonov et al., "Unbiased Average Age-Appropriate Atlases for Pediatric Studies," Neuroimage, vol. 54, No. 1, pp. 1-34 (Jan. 1, 2011).
Constantino, "The Quantitative Nature of Autistic Social Impairment," Pediatr Res., vol. 69, No. 5 Pt 2, pp. 1-17 (May 2011).
Hazlett et al., "Early Brain Overgrowth in Autism Associated with an Increase in Cortical Surface Area Before Age 2," Arch Gen Psychiatry, vol. 68, No. 5, pp. 1-20 (May 2011).
Constantino et al., "Infant head growth in male siblings of children with and without autism spectrum disorders," J. Neurodevelop Disord, vol. 2, pp. 39-46 (2010).
Fonov et al., "Improved Precision in the Measurement of Longitudinal Global and Regional Volumentric Changes Via a Novel MRI Gradient Distortion Characterization and Correction Technique," Computer Vision—ACCV 2006, Pt 1, vol. 6326, pp. 324-333 (2010).
Karmel et al., "Early Medical and Behavioral Characteristics of NICU Infants Later Classified With ASD," Pediatrics, vol. 126, No. 3, pp. 1-21 (Sep. 2010).
Dosenbach et al., "Prediction of Individual Brain Maturity Using fMRI," Science, vol. 329, No. 5997, pp. 1-9 (Sep. 10, 2010).
Power et al., "Methods to detect, characterize, and remove motion artifact in resting state fMRI," Neuroimage, vol. 84, pp. 1-45 (Jan. 2014).
Developmental Disabilities Monitoring Network, "Prevalence of Autism Spectrum Disorder Among Children Aged 8 Years—Autism and Developmental Disabilities Monitoring Network, 11 Sites, United States, 2010," Morbidity and Mortality Weekly Report, Surveillance Summaries, vol. 63, No. 2, pp. 1-24 (Mar. 28, 2014).
Marrus et al., "Lack of Effect of Risperidone on Core Autistic Symptoms: Data from a Longitudinal Study," Journal of Child Adolescent Psychopharmacology, vol. 24, No. 9, pp. 513-518 (2014).
Fang et al., "Overproduction of Upper-Layer Neurons in the Neocortex Leads to Autism-like Features in Mice," Cell Reports, vol. 9, pp. 1-10 (2014).
Power et al., "Spurious but systematic correlations in functional connectivity MRI networks arise from subject motion," Neuroimage, vol. 59, No. 3, pp. 1-28 (Feb. 1, 2012).
Philip et al., "A systematic review and meta-analysis of the fMRI investigation of autism spectrum disorders," Neuroscience and Biobehavioral Reviews, vol. 36, pp. 901-942 (2012).
Ozonoff et al., "Recurrence Risk for Autism Spectrum Disorders: A Baby Siblings Research Consortium Study," Pediatrics, vol. 128, No. 3, pp. e488-e495 (Sep. 2011).
Power et al., "Functional network organization of the human brain," Neuron, vol. 72, No. 4, pp. 1-25 (Nov. 17, 2011).
Kim et al., "Functions of GSK-3 signaling in development of the nervous system," Frontiers in Molecular Neuroscience, vol. 4, No. 44, pp. 1-13 (2011).
Piven, Specific Aims, NIH Research Project Grant Program Proposal, p. 1 (2011).
Hill et al., "Similar patterns of cortical expansion during human development and evolution," PNAS, vol. 107, No. 29, pp. 13135-13140 (Jul. 20, 2010).
Hinton, "A Practical Guide to Training Restricted Boltzmann Machines," UTML TR, pp. 1-21 (Aug. 2, 2010).
Dawson et al., "Randomized, Controlled Trial of an Intervention for Toddlers With Autism: The Early Start Denver Model," Pediatrics, vol. 125, pp. 1-15 (Jan. 2010).
Ozonoff et al., "A Prospective Study of the Emergence of Early Behavioral Signs of Autism," J Am Acad Child Adolesc Psychiatry, vol. 49, No. 3, pp. 1-18 (Mar. 2010).
Schumann et al., "Longitudinal MRI Study of Cortical Development through Early Childhood in Autism," J Neurosci, vol. 30, No. 12, pp. 1-24 (Mar. 24, 2010).
Tustison et al., "N4ITK: Improved N3 Bias Correction," IEEE Trans Med Imaging, vol. 29, No. 6, pp. 1-23 (Jun. 2010).
Winkler et al., "Cortical Thickness or Grey Matter Volume? The Importance of Selecting the Phenotype for Imaging Genetics Studies," Neuroimage, vol. 53, No. 3, pp. 1-28 (Nov. 15, 2010).
Mirenda et al., "Validating the Repetitive Behavior Scale-Revised in Young Children with Autism Spectrum Disorder," J. Autism Dev. Disord., vol. 40, pp. 1521-1530 (2010).
Piven, NIH Research Project Grant Program Proposal, pp. 1-19 (2010).
Piven, Response to Reviewers' Feedback, NIH Research Project Grant Program Proposal, p. 1 (2010).
Yirmiya et al., "The prodrome of autism: Early behavioral and biological signs, regression, peri- and post-natal development and genetics," Journal of Child Psychology and Psychiatry, vol. 51, pp. 1-89 (2010).
Shehzad et al., "The Resting Brain: Unconstrained yet Reliable," Cerebral Cortex, vol. 19, No. 10, pp. 2209-2229 (Oct. 2009).
Pereira et al., "Machine learning classifiers and fMRI: a tutorial overview," Neuroimage, vol. 45, pp. 1-24 (Mar. 2009).
Hastie et al., "The Elements of Statistical Learning: Data Mining, Inference and Prediction," Second Edition, Springer, pp. 1-764 (2009).
Lee et al., "Unsupervised feature learning for audio classification using convolutional deep belief networks," Advances in Neural Information Processing Systems (NIPS), pp. 1-9 (2009).
Lee et al., "Convolutional Deep Belief Networks for Scalable Unsupervised Learning of Hierarchical Representations," 26th Annual International Conference on Machine Learning (ICML), pp. 1-8 (2009).
Panizzon et al., "Distinct Genetic Influences on Cortical Surface Area and Cortical Thickness," Cerebral Cortex, vol. 19, pp. 2728-2735 (2009).

(56) References Cited

OTHER PUBLICATIONS

Shaw et al., "Neurodevelopmental Trajectories of the Human Cerebral Cortex," The Journal of Neuroscience, vol. 28, No. 14, pp. 3586-3594 (Apr. 2, 2008).
Im et al., "Brain Size and Cortical Structure in the Adult Human Brain," Cerebral Cortex, vol. 18, pp. 2181-2191 (Sep. 2008).
Avants et al., "Symmetric Diffeomorphic Image Registration with Cross-Correlation: Evaluating Automated Labeling of Elderly and Neurodegenerative Brain," Med Image Anal, vol. 12, No. 1, pp. 1-29 (Feb. 2008).
Knickmeyer et al., "A Structural MRI Study of Human Brain Development from Birth to 2 Years," J Neurosci, vol. 28, No. 47, pp. 1-17 (Nov. 19, 2008).
Ganz, "The Lifetime Distribution of the Incremental Societal Costs of Autism," Arch. Pediatr. Adolesc. Med., vol. 161, pp. 343-349 (Apr. 2007).
Gilmore et al., "Regional Gray Matter Growth, Sexual Dimorphism, and Cerebral Asymmetry in the Neonatal Brain," J Neurosci., vol. 27, No. 6, pp. 1-17 (Feb. 2007).
Piven, "III. Research Plan," PHS 398/2590, p. 238 (Apr. 2006).
Benjamini et al., "Adaptive Linear Step-up Procedures that control the False Discovery Rate," Biometricka, vol. 93, No. 3, pp. 1-25 (2006).
Casanova et al., "Minicolumnar abnormalities in autism," Acta Neuropathol, vol. 112, No. 3, pp. 287-303 (2006).
Hinton et al., "Reducing the Dimensionality of Data with Neural Networks," Science, vol. 313, pp. 504-507 (2006).
Hazlett et al., "Magnetic Resonance Imaging and Head Circumference Study of Brain Size in Autism: Birth Through Age 2 Years," Arch Gen Psychiatry, vol. 62, pp. 1366-1376 (2005).
Zou et al., "Regularization and variable selection via the elastic net," J of the Royal Statistical Society, Series B, Statistical Methodology, vol. 67, No. 2, pp. 301-320 (2005).
Zwaigenbaum et al., "Behavioral manifestations of autism in the first year of life," Int. J. Devl Neuroscience, vol. 23, pp. 143-152 (2005).
Mathias et al., "Algorithms for Spectral Analysis of Irregularly Sampled Time Series," Journal of Statistical Software, vol. 11, Issue 2, pp. 1-27 (May 2004).
Wetherby et al. "Early Indicators of Autism Spectrum Disorders in the Second Year of Life," Journal of Autism and Developmental Disorders, vol. 34, No. 5, pp. 473-493 (Oct. 2004).
Wetherby et al., "Validity and Reliability of the Communication and Symbolic Behavior Scales Developmental Profile With Very Young Children," Journal of Speech, Language, and Hearing Research, vol. 45, pp. 1202-1218 (Dec. 2002).
Chenn et al., "Regulation of Cerebral Cortical Size by Control of Cell Cycle Exit in Neural Precursors," Science, vol. 297, pp. 1-6 (2002).
Sparks et al., "Brain structural abnormalities in young children with autism spectrum disorder," Neurology, vol. 59, pp. 1-11 (2002).
Tzourio-Mazoyer et al., "Automated Anatomical Labeling of Activations in SPM Using a Macroscopic Anatomical Parcellation of the MNI MRI Single-Subject Brain," NeuroImage, vol. 15, pp. 273-289 (2002).
Courchesne et al., "Unusual brain growth patterns in early life in patients with autistic disorder: An MRI study," Neurology, vol. 57, pp. 245-254 (2001).
Wetherby et al., "Communication and Symbolic Behavior Scales Developmental Profile," Baltimore, MD: Paul H. Brookes, pp. 1-8 (2001).
Lord et al., "The Autism Diagnostic Observation Schedule-Generic: A Standard Measure of Social and Communication Deficits Associated with the Spectrum of Autism," Journal of Autism and Developmental Disorders, vol. 30, No. 3, pp. 205-223 (Jun. 2000).
Bodfish et al., "Varieties of Repetitive Behavior in Autism: Comparisons to Mental Retardation," Journal of Autism and Developmental Disorders, vol. 30, No. 3, pp. 237-243 (2000).
Giedd et al., "Brain development during childhood and adolescence: a longitudinal MRI study," Nature Neuroscience, vol. 2, pp. 1-3 (1999).
Friston et al., "Movement-related effects in fMRI time-series," Magn. Reson. Med., vol. 35, No. 3, pp. 1-28 (1996).
Cortes et al., "Support-Vector Networks," Machine Learning, vol. 20, No. 3, pp. 273-297 (1995).
Mullen, "Mullen Scales of Early Learning: AGS Edition," Circle Pines, MN: American Guidance Service, Inc., pp. 1-6 (Aug. 2015).
Piven et al., "An MRI Study of Brain Size in Autism," Am J Pyschiatry, vol. 152, pp. 1145-1149 (1995).
Rakic, "A small step for the cell, a giant leap for mankind: a hypothesis of neocortical expansion during evolution," Trends Neurosci, vol. 18, pp. 383-388 (1995).
Lord et al., "Autism Diagnostic Interview-Revised: A Revised Version of a Diagnostic Interview for Caregivers of Individuals with Possible Pervasive Developmental Disorders," Journal of Autism and Developmental Disorders, vol. 24, No. 5, pp. 659-685 (1994).
Piven et al., "Magnetic Resonance Imaging in Autism: Measurement of the Cerebellum, Pons, and Fourth Ventricle," Biol Psychiatry, vol. 31, pp. 491-504 (1992).
Fearnley et al., "Ageing and Parkinson's Disease: Substantia Nigra Regional Selectivity," Brain, vol. 114, pp. 2283-2301 (1991).
Autism Diagnostic Technology, "Transforming the Diagnosis of Autism," Wayback Machine, https://web.archive.org/web/20180804180716/http://autismdiagnostictechnology.com/, pp. 1-2 (Accessed Aug. 4, 2018).
Non-Final Office Action for U.S. Appl. No. 16/235,379 (dated Oct. 3, 2019).
Final Office Action for U.S. Appl. No. 16/235,379 (dated Apr. 20, 2020).
Li et al., "Measuring the dynamic longitudinal cortex development in infants by reconstruction of temporally consistent cortical surfaces," NeuroImage, vol. 90, pp. 266-279 (2014).
Jones et al., "Attention to eyes is present but in decline in 2-6 month-old infants later diagnosed with autism," Nature, vol. 504, pp. 427-431 (Dec. 2013).
Applicant-Initiated Interview Summary for U.S. Appl. No. 16/235,379 (dated Dec. 19, 2019).
Advisory Action for U.S. Appl. No. 16/235,379 (dated Jul. 1, 2020).
Applicant-Initiated Interview Summary for U.S. Appl. No. 16/235,379 (dated Jun. 29, 2020).
Non-Final Office Action for U.S. Appl. No. 16/235,379 (dated Jan. 6, 2021).
Examiner-Initiated Interview Summary for U.S. Appl. No. 16/235,379 (dated Apr. 19, 2021).
Final Office Action for U.S. Appl. No. 16/235,379 (dated Apr. 15, 2021).

* cited by examiner

| ASSESSMENT | N (ASD+/ASD-) | MEASURE | ASD-POS | ASD-NEG |
|---|---|---|---|---|
| SOCIAL-COMMUNICATION | 50 (8/42) | SOCIAL INTERACTION | 0.75 ± 0.3 | 2.51 ± 0.2 |
| SOCIAL-COMMUNICATION | 50 (8/42) | JOINT ATTENTION | 1.63 ± 0.6 | 3.66 ± 0.3 |
| COGNITIVE ABILITY | 57 (10/47) | EXPRESSIVE LANGUAGE | 18.91 ± 1.4 | 20.82 ± 0.6 |
| COGNITIVE ABILITY | 58 (11/47) | FINE MOTOR | 24.08 ± 1.0 | 23.84 ± 0.3 |
| COGNITIVE ABILITY | 53 (10/43) | GROSS MOTOR | 24.64 ± 0.5 | 25.79 ± 0.4 |
| COGNITIVE ABILITY | 57 (10/47) | VISUAL RECEPTION | 20.18 ± 2.0 | 23.58 ± 0.6 |
| COGNITIVE ABILITY | 58 (11/47) | RECEPTIVE LANGUAGE | 24.42 ± 0.8 | 26.53 ± 0.5 |
| REPETITIVE BEHAVIOR | 47 (9/38) | SELF-INJURIOUS | 2.3 ± 1.0 | 0.16 ± 0.1 |
| REPETITIVE BEHAVIOR | 47 (9/38) | STEREOTYPED | 3.4 ± 0.8 | 0.31 ± 0.1 |
| REPETITIVE BEHAVIOR | 47 (9/38) | SAMENESS | 4.9 ± 0.9 | 0.9 ± 0.2 |
| REPETITIVE BEHAVIOR | 47 (9/38) | RITUALISTIC | 2.2 ± 0.5 | 0.5 ± 0.1 |
| REPETITIVE BEHAVIOR | 47 (9/38) | COMPULSIVE | 3.4 ± 0.4 | 0.4 ± 0.1 |
| REPETITIVE BEHAVIOR | 47 (9/38) | REPETITIVE | 1.8 ± 0.9 | 0.41 ± 0.1 |

FIG. 1

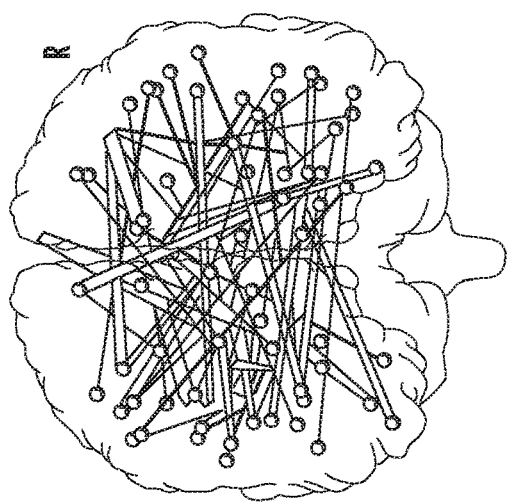
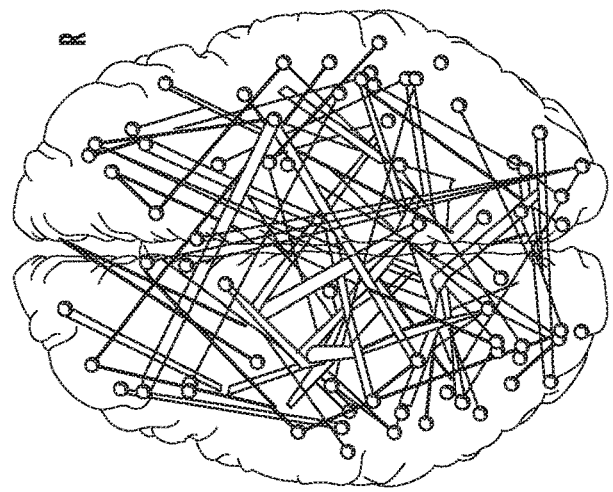
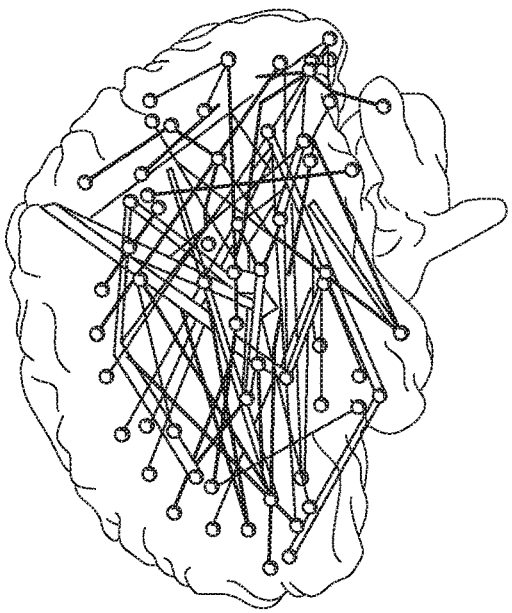
C) REPETITIVE BEHAVIOR
FIG. 4C

| | ROI1 | | | ROI2 | | | AVERAGE R-VALUE | | t-VALUE | p-VALUE |
|---|---|---|---|---|---|---|---|---|---|---|
| 600 | X | Y | Z | X | Y | Z | HR-POS | HR-NEG | | |
| CSBS | 46 | -45 | 44 | -52 | -25 | 41 | 0.391 | 0.132 | -3.0963 | 0.003 |
| | -50 | 0 | -24 | 8 | -48 | 69 | 0.113 | -0.062 | -2.9325 | 0.0048 |
| | -21 | 4 | -2 | 8 | -48 | 69 | -0.261 | -0.019 | 4.3423 | 0.0001 |
| | -48 | -66 | -8 | 51 | -31 | 34 | 0.357 | 0.137 | -3.2171 | 0.0021 |
| | -43 | -65 | 31 | -47 | -28 | 5 | -0.135 | 0.054 | 2.9743 | 0.0043 |
| | -9 | 10 | 10 | -47 | -28 | 5 | 0.109 | -0.069 | -3.6864 | 0.0005 |
| | -33 | 49 | 9 | -51 | -24 | 22 | 0.132 | -0.059 | -3.1777 | 0.0024 |
| | -11 | -93 | -15 | -3 | -50 | 12 | -0.231 | -0.034 | 3.0045 | 0.0039 |
| | 56 | -8 | -2 | 11 | 30 | 24 | 0.116 | -0.081 | -3.2679 | 0.0018 |
| | 26 | -39 | -11 | 50 | -6 | -12 | 0.236 | 0.008 | -3.6447 | 0.0006 |
| | -25 | -89 | 0 | 44 | -52 | 28 | 0.153 | -0.043 | -2.9257 | 0.0049 |
| | 20 | -70 | -9 | -47 | -43 | 0 | 0.102 | -0.138 | -3.9104 | 0.0002 |
| | -47 | -9 | -36 | 17 | -48 | -9 | 0.091 | -0.111 | -3.6725 | 0.0005 |
| | 39 | -5 | 48 | 19 | -66 | 1 | -0.192 | 0.003 | 3.1196 | 0.0028 |
| | 39 | -5 | 48 | -17 | -68 | 3 | -0.205 | -0.043 | 3.023 | 0.0037 |
| | 39 | -39 | -20 | 26 | 4 | -4 | -0.249 | -0.069 | 3.0731 | 0.0032 |
| MSEL | -41 | -56 | 41 | 26 | -96 | -15 | -0.120 | 0.059 | 2.9743 | 0.0043 |
| | 4 | 18 | 39 | 26 | -96 | -15 | 0.039 | -0.108 | -3.0157 | 0.0038 |
| | 29 | 49 | 20 | 53 | -33 | -14 | 0.248 | 0.027 | -3.0839 | 0.0031 |
| | -26 | -71 | 33 | -8 | -54 | 57 | 0.347 | 0.152 | -3.0113 | 0.0039 |
| | 17 | -79 | -34 | -52 | -25 | 41 | -0.125 | 0.078 | 2.9314 | 0.0048 |
| | 52 | -47 | 36 | -52 | -25 | 41 | 0.162 | -0.065 | -3.7255 | 0.0004 |
| | -10 | -21 | 8 | -44 | -34 | 44 | -0.207 | -0.046 | 2.9882 | 0.0041 |
| | 11 | -20 | 9 | -44 | -34 | 44 | -0.247 | -0.055 | 3.8033 | 0.0004 |
| | -40 | 40 | 2 | 51 | -31 | 34 | 0.293 | 0.039 | -3.4717 | 0.001 |
| | -48 | -66 | -8 | 51 | -31 | 34 | 0.357 | 0.137 | -3.2171 | 0.0021 |
| | 14 | -64 | 24 | 62 | -36 | 21 | 0.157 | -0.033 | -2.9463 | 0.0047 |
| | -44 | -61 | 18 | -47 | -28 | 5 | -0.059 | 0.189 | 4.1552 | 0.0001 |
| | -43 | -65 | 31 | -47 | -28 | 5 | -0.135 | 0.054 | 2.9743 | 0.0043 |
| | -48 | -66 | -8 | 56 | -21 | 30 | 0.237 | 0.039 | -3.1136 | 0.0029 |

FROM FIG. 6A1

| | | | | | | | | | |
|---|---|---|---|---|---|---|---|---|---|
| -8 | -80 | 5 | -29 | -29 | 12 | 0.135 | -0.029 | -3.2171 | 0.0021 |
| -14 | -72 | -9 | -29 | -29 | 12 | 0.155 | -0.026 | -3.5678 | 0.0007 |
| -30 | -14 | 1 | -29 | -29 | 12 | 0.402 | 0.106 | -4.5618 | <.0001 |
| -10 | -21 | 8 | -39 | -75 | 22 | -0.001 | -0.192 | -3.1934 | 0.0023 |
| -4 | 21 | 46 | -43 | -65 | 31 | 0.084 | -0.090 | -2.9371 | 0.0048 |
| -11 | -93 | -15 | -3 | -50 | 12 | -0.231 | -0.034 | 3.0045 | 0.0039 |
| 19 | -85 | -4 | 14 | -64 | 24 | -0.159 | 0.049 | 3.1065 | 0.0029 |
| 19 | -85 | -4 | 28 | -76 | -31 | 0.223 | 0.005 | -3.4512 | 0.0011 |
| 22 | -58 | -22 | -44 | 27 | -9 | -0.221 | -0.032 | 3.1342 | 0.0027 |
| 39 | -5 | 48 | 23 | 39 | -9 | 0.168 | -0.039 | -3.4365 | 0.0011 |
| 39 | -5 | 48 | 32 | 48 | -6 | 0.154 | -0.014 | -3.3451 | 0.0015 |
| 23 | -60 | 57 | 39 | -5 | 48 | 0.243 | -0.047 | -4.043 | 0.0002 |
| 26 | -9 | 54 | -10 | -21 | 8 | -0.246 | -0.028 | 3.2268 | 0.0021 |
| -53 | -41 | 12 | 27 | -3 | 7 | 0.095 | -0.099 | -2.9981 | 0.004 |
| 20 | -70 | -9 | -47 | -9 | -36 | 0.045 | -0.145 | -3.1499 | 0.0026 |

| | | | | | | | | | | |
|---|---|---|---|---|---|---|---|---|---|---|
| RBS-R | 32 | 33 | -6 | -23 | -96 | -15 | -0.106 | 0.105 | 2.9824 | 0.0042 |
| | 5 | 3 | 51 | 26 | -96 | -15 | 0.062 | -0.098 | -2.9271 | 0.0049 |
| | -41 | -56 | 41 | 26 | -96 | -15 | -0.120 | 0.059 | 2.9743 | 0.0043 |
| | -4 | 21 | 46 | 26 | -96 | -15 | 0.084 | -0.085 | -2.9766 | 0.0043 |
| | 4 | 18 | 39 | 26 | -96 | -15 | 0.039 | -0.108 | -3.0157 | 0.0038 |
| | 29 | 49 | 20 | 53 | -33 | -14 | 0.248 | 0.027 | -3.0839 | 0.0031 |
| | -25 | -89 | 0 | 32 | 33 | -6 | -0.135 | 0.122 | 3.6749 | 0.0005 |
| | 19 | -85 | -4 | -8 | -54 | 57 | -0.256 | -0.028 | 3.885 | 0.0003 |
| | -26 | -71 | 33 | -8 | -54 | 57 | 0.347 | 0.152 | -3.0113 | 0.0039 |
| | -40 | 40 | 2 | -52 | -25 | 41 | 0.261 | 0.026 | -3.1149 | 0.0029 |
| | -21 | 4 | -2 | 8 | -48 | 69 | -0.261 | -0.019 | 4.3423 | 0.0001 |
| | -30 | -14 | 1 | 8 | -48 | 69 | -0.324 | -0.112 | 3.7371 | 0.0004 |
| | 52 | -47 | 36 | -39 | -22 | 52 | -0.005 | -0.193 | -3.1362 | 0.0027 |
| | -27 | -79 | 16 | 26 | -42 | 57 | 0.114 | -0.107 | -3.0675 | 0.0033 |
| | -41 | 20 | 31 | 47 | -24 | 42 | 0.143 | -0.047 | -2.9331 | 0.0048 |
| | -10 | -21 | 8 | -44 | -34 | 44 | -0.207 | -0.046 | -2.9882 | 0.0041 |
| | 11 | -20 | 9 | -44 | -34 | 44 | -0.247 | -0.055 | 3.8033 | 0.0004 |
| | -48 | -66 | -8 | 51 | -31 | 34 | 0.357 | 0.137 | -3.2171 | 0.0021 |

FIG. 6A2

| | | | | | | | | | |
|---|---|---|---|---|---|---|---|---|---|
| -40 | -60 | -10 | 47 | 4 | 3 | 0.074 | -0.111 | -3.3945 | 0.0013 |
| 5 | 60 | 3 | -33 | 0 | 6 | -0.292 | -0.098 | 3.4086 | 0.0012 |
| 27 | -3 | 7 | 62 | -36 | 21 | 0.088 | -0.098 | -3.1735 | 0.0024 |
| -9 | 10 | 10 | -58 | -27 | 13 | 0.097 | -0.092 | -3.0845 | 0.0031 |
| -14 | -72 | -9 | -47 | -28 | 5 | 0.144 | -0.017 | -3.1967 | 0.0023 |
| -9 | 10 | 10 | -47 | -28 | 5 | 0.109 | -0.069 | -3.6864 | 0.0005 |
| -33 | 49 | 9 | -51 | -24 | 22 | 0.132 | -0.059 | -3.1777 | 0.0024 |
| -40 | 40 | 2 | -51 | -24 | 22 | 0.269 | 0.013 | -3.5744 | 0.0007 |
| -3 | 36 | 20 | -53 | -12 | 12 | 0.138 | -0.061 | -3.2215 | 0.0021 |
| -23 | -90 | 15 | -53 | -12 | 12 | 0.079 | -0.124 | -3.3904 | 0.0013 |
| -33 | 49 | 9 | 56 | -21 | 30 | 0.161 | -0.038 | -3.2002 | 0.0022 |
| -8 | -80 | 5 | -29 | -29 | 12 | 0.135 | -0.029 | -3.2171 | 0.0021 |
| 22 | 6 | 5 | -29 | -29 | 12 | 0.227 | 0.049 | -2.9249 | 0.0049 |
| -30 | -14 | 1 | -29 | -29 | 12 | 0.402 | 0.106 | -4.5618 | <.0001 |
| -23 | -90 | 15 | -39 | -75 | 22 | -0.141 | 0.117 | 3.1456 | 0.0026 |
| -30 | -14 | 1 | 5 | 60 | 3 | -0.229 | -0.040 | 3.3357 | 0.0015 |
| -53 | -41 | 12 | 8 | 42 | -9 | 0.212 | 0.027 | -2.9973 | 0.004 |
| -41 | 9 | -30 | -17 | 57 | -3 | 0.132 | -0.107 | -3.5593 | 0.0008 |
| 51 | -45 | 22 | -44 | -61 | 18 | 0.142 | 0.399 | 3.5378 | 0.0008 |
| 49 | -31 | -2 | -44 | -61 | 18 | 0.130 | 0.344 | 3.2382 | 0.002 |
| -26 | -71 | 33 | -44 | -61 | 18 | 0.249 | 0.036 | -3.0366 | 0.0036 |
| -17 | -68 | 3 | -41 | 9 | -30 | 0.145 | -0.072 | -3.5503 | 0.0008 |
| 36 | 37 | 20 | 44 | 12 | -24 | -0.003 | -0.197 | -3.0982 | 0.003 |
| 50 | 3 | -24 | -55 | -27 | -14 | 0.224 | 0.439 | 2.9337 | 0.0048 |
| 56 | -54 | -12 | 26 | 12 | -12 | 0.064 | -0.098 | -2.9917 | 0.0041 |
| 50 | 27 | 6 | 5 | -60 | 33 | 0.141 | -0.029 | -3.4505 | 0.0011 |
| 8 | -72 | 9 | -3 | -50 | 12 | -0.175 | 0.045 | 3.0276 | 0.0037 |
| 6 | -81 | 4 | -3 | -50 | 12 | -0.237 | -0.012 | 3.4234 | 0.0012 |
| 19 | -66 | 1 | -3 | 32 | 39 | -0.293 | -0.118 | 3.2029 | 0.0022 |

FROM FIG. 6B1

| | | | | | | | | | |
|---|---|---|---|---|---|---|---|---|---|
| 24 | 43 | 31 | 11 | 30 | 24 | -0.0042 | 0.178 | 3.0643 | 0.0033 |
| 56 | -8 | -2 | 11 | 30 | 24 | 0.116 | -0.081 | -3.2679 | 0.0018 |
| 26 | -39 | -11 | 50 | -6 | -12 | 0.236 | 0.008 | -3.6447 | 0.0006 |
| 19 | -85 | -4 | 28 | -76 | -31 | 0.223 | 0.005 | -3.4512 | 0.0011 |
| 20 | -70 | -9 | -47 | -43 | 0 | 0.102 | -0.138 | -3.9104 | 0.0002 |
| 56 | -8 | -2 | -7 | -72 | 38 | -0.192 | -0.033 | 3.0628 | 0.0033 |
| -29 | -12 | -33 | 10 | -67 | 39 | -0.264 | -0.061 | 3.2248 | 0.0021 |
| 49 | -31 | -2 | 8 | -90 | -9 | 0.155 | -0.044 | -3.2011 | 0.0022 |
| 19 | -85 | -4 | 17 | -90 | -15 | 0.654 | 0.408 | -3.1895 | 0.0023 |
| -47 | -9 | -36 | 17 | -48 | -9 | 0.091 | -0.111 | -3.6725 | 0.0005 |
| 39 | -5 | 48 | 19 | -66 | 1 | -0.192 | 0.003 | 3.1196 | 0.0028 |
| 12 | -78 | 38 | -23 | -90 | 15 | -0.057 | 0.197 | 3.2124 | 0.0022 |
| 32 | 48 | -6 | -17 | -68 | 3 | -0.205 | -0.027 | 3.109 | 0.0029 |
| 39 | -5 | 48 | -17 | -68 | 3 | -0.205 | -0.043 | 3.023 | 0.0037 |
| 32 | 48 | -6 | -15 | -53 | -2 | -0.237 | -0.042 | 3.0124 | 0.0039 |
| -53 | -41 | 12 | -15 | -53 | -2 | 0.166 | -0.023 | -2.9303 | 0.0049 |
| -38 | -87 | -9 | 25 | -79 | -16 | 0.433 | 0.164 | -3.7706 | 0.0004 |
| 49 | -35 | 9 | 25 | -79 | -16 | 0.071 | -0.102 | -3.0357 | 0.0036 |
| 44 | -60 | 4 | -3 | -81 | 18 | 0.183 | -0.029 | -3.096 | 0.003 |
| 35 | -84 | 11 | -38 | -87 | -9 | 0.370 | 0.109 | -3.4985 | 0.0009 |
| 26 | -9 | 54 | -25 | -89 | 0 | 0.132 | -0.063 | -3.1446 | 0.0026 |
| 24 | 43 | 31 | -31 | -78 | -15 | -0.216 | -0.033 | 3.2775 | 0.0018 |
| 22 | -58 | -22 | -51 | -50 | 39 | -0.036 | -0.213 | -3.2502 | 0.0019 |
| 39 | -5 | 48 | 32 | 48 | -6 | 0.154 | -0.014 | -3.3451 | 0.0015 |
| 39 | -5 | 48 | -41 | 33 | 24 | 0.277 | -0.031 | -4.3877 | 0.0001 |
| -32 | -48 | 44 | 39 | -5 | 48 | 0.218 | -0.030 | -3.7165 | 0.0005 |
| -32 | -48 | 44 | 11 | -20 | 9 | -0.317 | -0.145 | 3.6126 | 0.0006 |
| 39 | -39 | -20 | -21 | 4 | -2 | -0.279 | -0.070 | 3.4365 | 0.0011 |
| -53 | -41 | 12 | -30 | -14 | 1 | 0.077 | -0.116 | -3.3052 | 0.0016 |
| 20 | -70 | -9 | -47 | -9 | -36 | 0.045 | -0.145 | -3.1499 | 0.0026 |
| 39 | -39 | -20 | 26 | 4 | -4 | -0.249 | -0.069 | 3.0731 | 0.0032 |

|  |  | AVERAGES | | | |
| --- | --- | --- | --- | --- | --- |
|  |  | PRIMARY COHORT | ADDITIONAL COHORT | $t$-VALUE | $p$-VALUE |
| CSBS | SOCIAL INTERACTION | 2.14 | 2.33 | 0.61 | 0.54 |
| CSBS | JOINT ATTENTION | 3.30 | 3.20 | 0.27 | 0.79 |
| MSEL | EXPRESSIVE LANGUAGE | 20.98 | 21.41 | 0.48 | 0.63 |
| MSEL | FINE MOTOR | 24.10 | 23.97 | 0.30 | 0.76 |
| MSEL | GROSS MOTOR | 25.89 | 25.15 | 1.59 | 0.11 |
| MSEL | RECEPTIVE LANGUAGE | 23.35 | 23.25 | 0.10 | 0.92 |
| MSEL | VISUAL RECEPTION | 26.74 | 27.74 | 1.31 | 0.19 |
| RBS-R | STEREOTYPED | 0.91 | 1.22 | 0.74 | 0.46 |
| RBS-R | SELF-INJURIOUS | 0.64 | 0.84 | 0.63 | 0.53 |
| RBS-R | COMPULSIVE | 0.96 | 0.80 | 0.33 | 0.74 |
| RBS-R | RITUALISTIC | 0.79 | 0.67 | 0.28 | 0.78 |
| RBS-R | SAMENESS | 1.60 | 1.43 | 0.26 | 0.80 |
| RBS-R | RESTRICTED | 0.47 | 0.86 | 1.33 | 0.19 |

FIG. 7

METHODS, SYSTEMS, AND COMPUTER READABLE MEDIA FOR UTILIZING FUNCTIONAL CONNECTIVITY BRAIN IMAGING FOR DIAGNOSIS OF A NEUROBEHAVIORAL DISORDER

PRIORITY CLAIM

This application is a continuation of International Application No. PCT/US17/40032, which claims the priority benefit of U.S. Provisional Patent Application Ser. No. 62/356,485, filed Jun. 29, 2016, the disclosures of which are incorporated by reference herein in their entireties.

GOVERNMENT INTEREST

This invention was made with government support under Grant Nos. MH093510, HD055741 and HD040127 awarded by the National Institutes of Health. The government has certain rights in the invention.

TECHNICAL FIELD

The subject matter described herein relates to medical imaging analysis. More specifically, the subject matter relates to methods, systems, and computer readable media for utilizing functional connectivity brain imaging for diagnosis of a neurobehavioral disorder.

BACKGROUND

Despite tremendous research efforts, autism still confers substantial burden to affected individuals, their families, and the community. Early intervention is critical, but the earliest we can currently diagnose autism via observational/behavioral criteria is 24 month or later. Further, such diagnosis depends on a subjective clinical evaluation of behaviors that begin to emerge around this time.

SUMMARY

Methods, systems, and computer readable media for utilizing functional connectivity brain imaging for diagnosis of a neurobehavioral disorder are disclosed. One method for utilizing functional connectivity brain imaging for diagnosis of a neurobehavioral disorder includes receiving brain imaging data for a human subject of a first age, wherein the brain imaging data includes functional connectivity magnetic resonance imaging (fcMRI) data, and predicting, using at least one functional connection between brain locations in the fcMRI data, a neurobehavioral disorder diagnosis for the subject at a second age greater than the first age.

A system for utilizing functional connectivity brain imaging for diagnosis of a neurobehavioral disorder is also disclosed. The system comprises at least one processor and a neurobehavioral disorder diagnosis module (ADM) implemented using the at least one processor. The ADM is configured for receiving brain imaging data for a human subject of a first age, wherein the brain imaging data includes fcMRI data and for predicting, using at least one functional connection between brain locations in the fcMRI data, a neurobehavioral disorder diagnosis for the subject at a second age greater than the first age.

The subject matter described herein can be implemented in software in combination with hardware and/or firmware. For example, the subject matter described herein can be implemented in software executed by at least one processor.

In one example implementation, the subject matter described herein may be implemented using at least one computer readable medium having stored thereon computer executable instructions that when executed by at least one processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As used herein, the terms "node" and "host" refer to a physical computing platform or device including one or more processors and memory.

As used herein, the terms "function" and "module" refer to software in combination with hardware and/or firmware for implementing features described herein.

BRIEF DESCRIPTION OF THE DRAWINGS

Some embodiments of the subject matter described herein will now be explained with reference to the accompanying drawings, wherein like reference numerals represent like parts, of which:

FIG. 1 depicts average scores for various behavior assessments;

FIGS. 4A-C depict functional connectivity associated with various behaviors;

FIGS. 6A-B depict Talairach coordinates for regions of interest depicted in FIGS. 4A-C;

FIG. 7 depicts average scores between two high-risk groups;

DETAILED DESCRIPTION

Figure 2:
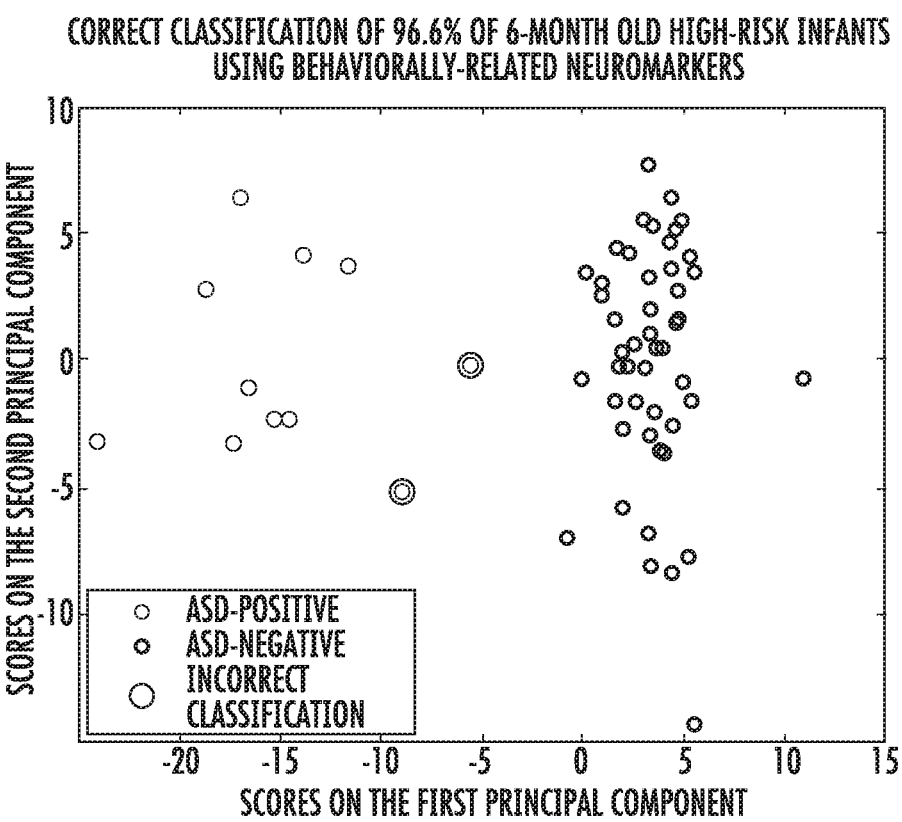
FIG. 2 depicts classifications of 6-month old high-risk infants using an example detection technique that utilizes functional connectivity brain imaging.

The subject matter described herein involves methods, systems, and computer readable media for utilizing functional connectivity brain imaging for diagnosis of a neurobehavioral disorder. Reference will now be made in detail to various embodiments of the subject matter described herein, examples of which are illustrated in the accompanying drawings. Wherever possible, the same reference numbers will be used throughout the drawings to refer to the same or like parts.

Autism spectrum disorder (ASD) is a neurodevelopmental disorder characterized by deficits in social behavior and the presence of restrictive and repetitive behaviors (1). It is estimated that 1 in 68 children are affected by the disorder (2) and, despite tremendous research efforts, ASD still confers substantial burden to affected individuals, their families, and the community (3, 4). Intervention is critically important, and there is a general consensus that early detection paired with early intervention would have a significant impact on improving outcomes (5-7).

One barrier to early (i.e., prior to 24 months) detection is that the defining behavioral characteristics of ASD generally unfold during the second year of life, typically showing consolidation of the full behavioral syndrome around 24 months or later (8, 9). Behavioral differences of ASD have been observed as early as six months of age in characteristics such as gross motor ability, visual reception, and patterns of eye tracking (10-14); however, these associated characteristics have not been able to predict which children will later receive a diagnosis. Given the known plasticity in brain and behavior during the first year of life, together with the absence of the defining features of the disorder, intervention during this presymptomatic phase, prior to consolidation of the full syndrome of ASD, is likely to show considerably stronger benefits compared with later treatments (5).

Research on neurodegenerative disorders has shown that changes in the brain are often seen preceding clinical manifestations. For example, in Parkinson's disease, approximately 50 percent of the neurons in the substantia nigra are lost before clinical features become apparent (15). This suggests that brain-related changes appear earlier than behavioral changes and may be useful in predicting future behavioral diagnosis. In ASD, a number of selected morphological (16-18) and electrophysiological (19) brain differences have been reported as early as six months of age in infants later diagnosed with ASD; however, the reported group differences in these specific brain structures have not yet shown the sensitivity and specificity required to be effective for the early detection of ASD.

Given the complexity and heterogeneity of ASD, methods for early detection of ASD using brain metrics will likely require information that is multivariate, complex, and developmentally sensitive. Recent research using fcMRI has linked the functional organization of the human brain to individual cognitive profiles (20-22). These measures of brain functional connectivity are reliable (23) and can accommodate participants as young as neonates (24). Furthermore, in conjunction with machine learning approaches, fcMRI data has provided predictions of brain maturation (25, 26) and diagnostic category (27-32) at the single-subject level. By training machine learning algorithms to identify underlying pattern differences between group data, researchers have been able to predict the group membership of an independent individual (33). In the present study we postulated that brain functional connectivity at 6 months of age would capture the complexity of ASD and provide a robust method for predicting later diagnosis. Our results revealed that that machine learning, applied to fcMRI data at 6 months of age in infants at high familial risk for ASD can accurately predict an ASD diagnosis at 24 months of age.

Results

A high-familial-risk-for-ASD cohort of 59 infants was included in this study: 11 ASD-positive or ASD-pos (diagnosed with ASD at 24 months) and 48 ASD-negative or ASD-neg (non-ASD at 24 months). Prospective neuroimaging data were collected from each infant at 6 months of age while they were naturally sleeping. Cognitive, behavioral, and diagnostic assessments, as described below were, completed at their 24-month follow-up visit.

Identification of Brain-behavior Features

Brain-behavior correlations were computed with each participant's 24-month assessment scores of social interactions, communication, motor development, and repetitive behavior. FIG. 1 depicts scores for various behavior assessments. In particular, table 100 of FIG. 1 shows the average raw scores and standard error for each of these behavioral measures by group. Whole-brain functional connectivity matrices were created using a set of 230 functionally-defined regions of interest using each participant's functional MRI data from their 6-month visit. This resulted in 26,335 pairs of regions used for further analysis. The correlations between 24-month behavioral scores and each participant's 6-month functional connectivity data were used to define a feature space across all subjects using cross-validation. This resulted in a total of 974 functional connections in the 6-month-old brain that showed a relationship with behavior at 24-months. Together these functional connections constitute <4% of the potential 26,335 total functional connections studied. Participants' scores on the first and second principal components of this feature space were plotted against each other in FIG. 2, revealing an evident linear separation between the ASD-pos and ASD-neg groups.

FIG. 2 is a diagram 200 that depicts classifications of 6-month old high-risk infants using an example detection technique utilizing functional connectivity brain imaging. As shown, FIG. 2 shows a correct classification of 96.6% of 6-month old high-risk infants. ASD-positive (light gray) and ASD-negative (dark gray) subjects are shown with their score on first principal component of brain-behavior variance on the x-axis, and the second component on the y-axis. The two subjects that were incorrectly classified in the leave-one-out nested cross-validation analysis are circled, showing two subjects who are ASD-positive but were classified as ASD-negative.

Predicting Individual 24-Month Clinical Diagnoses

To determine whether or not 6-month functional connectivity features were capable of predicting the clinical diagnostic outcome of an individual infant, we used a fully cross-validated approach with a "nested" leave-one-out procedure. This procedure (detailed in the Materials and Methods) allowed each infant to be predicted independently, without being used to define features or build the classifier.

Figure 3:
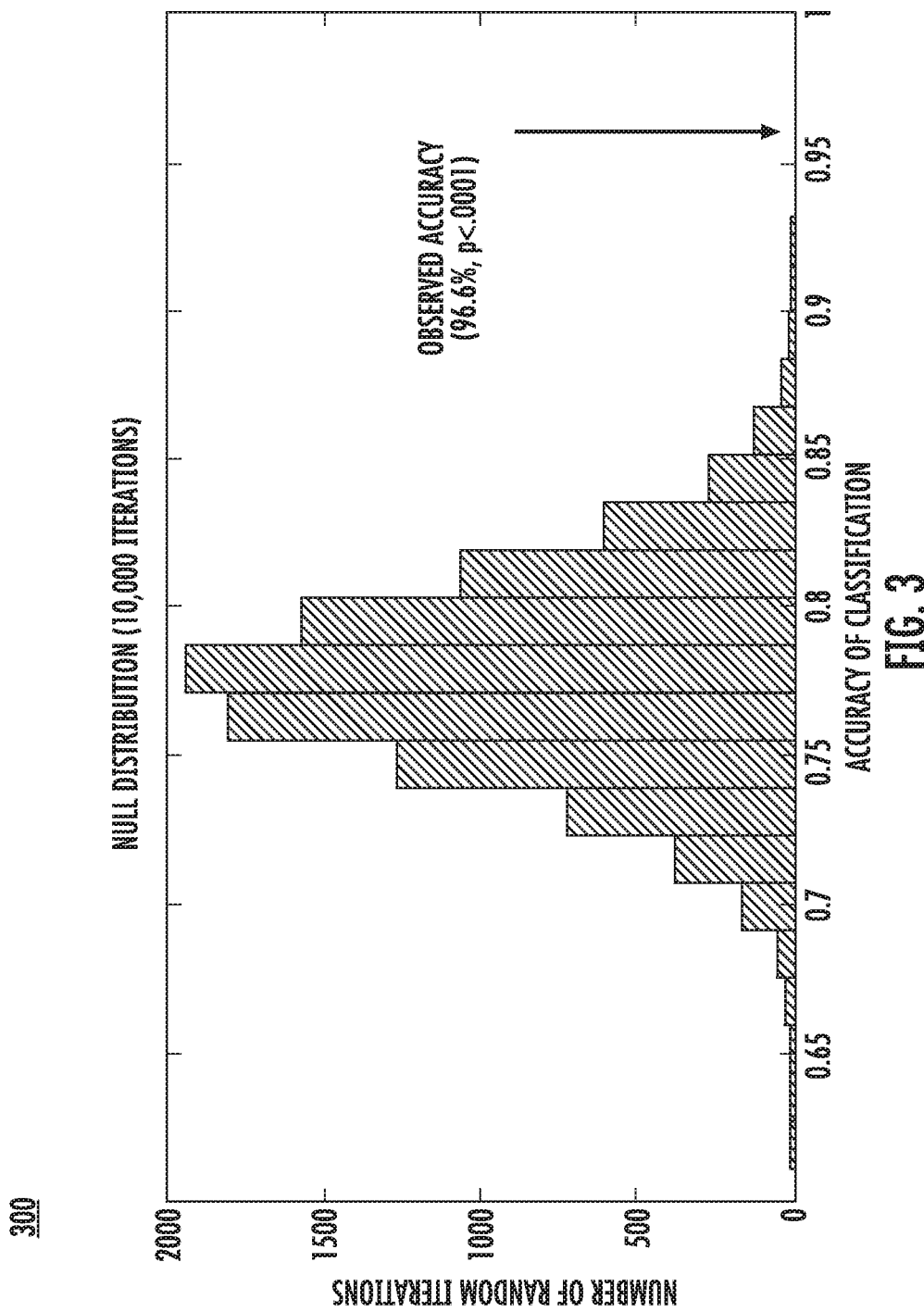
FIG. 3 depicts a null distribution of classification accuracy.
Figure 4A:
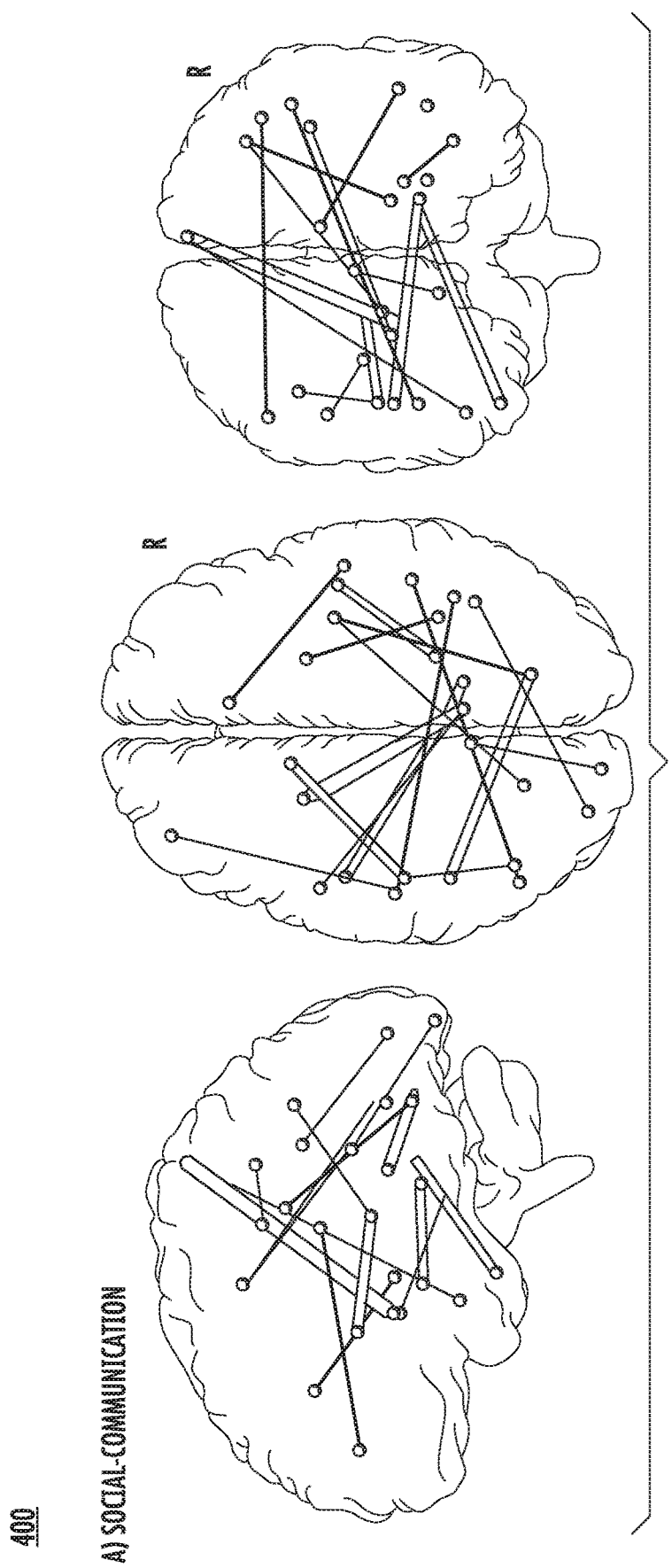
Figure 4B:
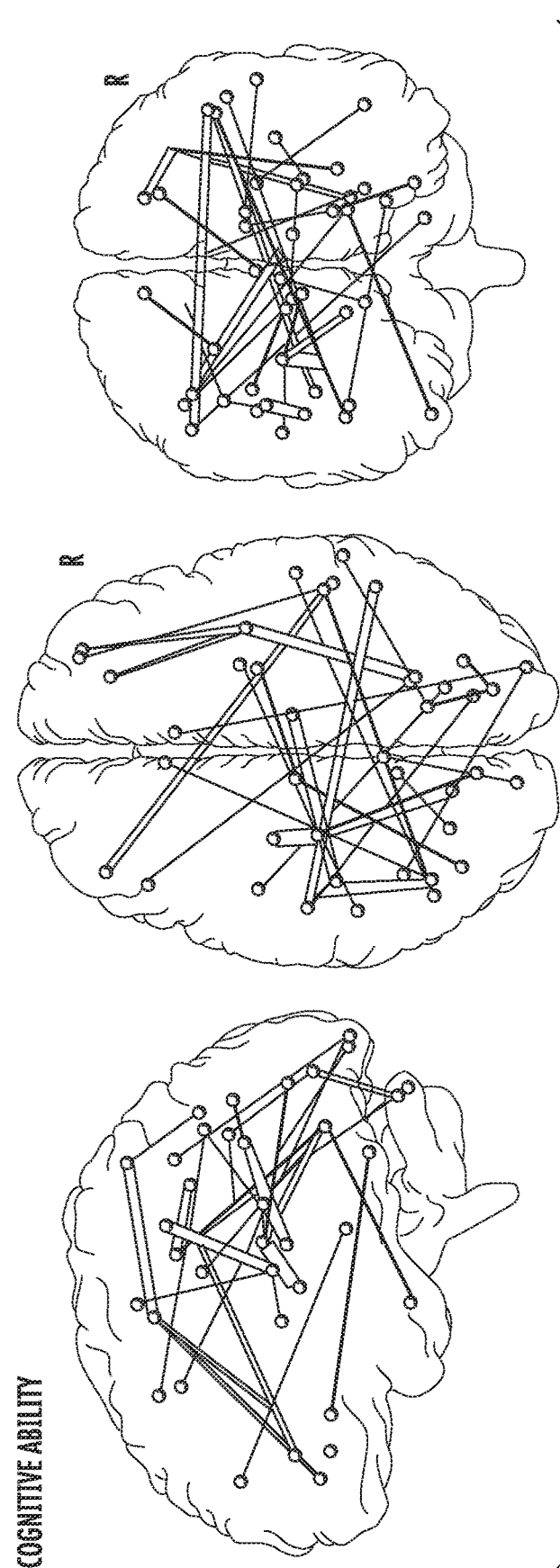

The classification accuracy using functional connectivity data in 6-month old infants was 96,6% (95% CI 87,3-99.4, p<0.001). FIG. 3 is a diagram 300 that marks the observed accuracy of this classification analysis against the null distribution generated using randomized diagnosis labels (see Materials and Methods). As shown in FIG. 3, the bars represent the number of random iterations at each level of accuracy. The arrow marks the observed accuracy from the nested leave-one-out cross-validation classification analysis, corresponding to a p-value of p<0.0001. Sensitivity of this approach was 81.8% (95% CI 47.8-96.8) and specificity was 100% (95% CI 90.8-100). The probability that subjects with a positive classification truly had ASD (positive predictive value) at 24 months was 100% (95% CI 62.9-100). The probability that subjects with a negative classification did not have ASD (negative predictive value) at 24 months was 96.0 (95% CI 85.1-99.3). FIGS. 4A-C show a subset of the regions used in the classifier analysis that show reduced or increased functional connectivity in 6-month-old infants who develop ASD.

FIG. 4A is a diagram 400 that represents the functional connections that show a relationship to assessment scores associated with social communication listed in Table 100 of FIG. 1. FIG. 4B is a diagram 402 that represents the functional connections that show a relationship to assessment scores associated with cognitive ability listed in Table 100 of FIG. 1. FIG. 4C is a diagram 404 that represents the functional connections that show a relationship to assessment scores associated with repetitive behavior listed in Table 100 of FIG. 1. Additional details of the assessments as well as the specific items and subscales are included in the Materials and Methods. For each assessment, the functional connections associated with individual measures were combined and projected onto a Talairach brain. The color and thickness of each connection signifies the sign and strength of the t-value it represents. Unpaired two-sample t-tests were used to test the difference between group means (ASD-pos vs ASD-neg). A light gray bar/line signifies a connection that shows more negative connectivity in the ASD-pos group on average, while a dark gray line/bar signifies more positive connectivity. T-values were set to a threshold of $p<0.005$, uncorrected, and the thickness of each bar represents its strength. FIGS. 6A-B depict Talairach coordinates for regions of interest depicted in FIGS. 4A-C. These calculations are for visualization and should not be interpreted as differences directly contributing to any individual's classification.

Leave-10-Out

In order to test the generalizability and validity of our results, we used a similar classification analysis with a greater number of subjects held independent (leave-10-out), to show that our results were fairly robust. On average, the leave-ten-out analysis performed with 92.7±0.7% accuracy, indicating that it correctly predicted between nine and ten of the ten independent subjects for the majority of the 1000 iterations and was nearly as accurate as the nested leave-one-out analysis. Based on the null distribution (described in the Materials and Methods), this approximately corresponds to a p-value of <0.001. This result suggests that the classifier may be able to generalize to new samples of infants and is fairly robust.

Random Features

To ensure that the identified brain-behavior features were meaningfully related to clinical outcomes, we tested whether or not the SVM could accurately classify the sample of subjects if given a random set of brain-behavior features. To do this, we replaced the features chosen in the nested feature detection step with the same number of features selected at random. With 1000 iterations of randomly selected functional connections, the average accuracy of the classifier was 81.1±0.9%. Based on the null distribution (described in the Materials and Methods), this approximately corresponds to a p-value of $p=0.23$. This result suggests that the behaviorally-related features are better able to classify ASD outcomes than unrelated functional connections.

Discussion

The public health importance of ASD has been increasingly recognized over the last 15-20 years (2, 3). Treatment studies have shown modest effects in improving the core characteristics of ASD (34, 35). Research on infants at high familial risk for ASD has revealed a seemingly narrow window of opportunity, prior to age 24 months, when intervention may have the potential to ameliorate the unfolding of the core features of this disorder (5, 6). Intervention studies with high-familial-risk infants (6, 7) suggest that behavioral intervention in the latter part of the first, and early second years, may be more effective than later (post-diagnosis) intervention. Unfortunately, early behavioral markers have not had sufficient power as predictors of later diagnosis to be clinically useful and so, to date, methods for early, presymptomatic detection have not been available.

Our results suggest that early brain metrics, identified on the basis of their association with later ASD-related behaviors, are able to accurately predict an individual infant's 24 month diagnosis of ASD, by six months of age. We focused on predicting diagnostic outcome at 24 months of age, a time when the full syndrome of ASD begins to consolidate and can be reliably diagnosed (8, 9). In this study, functional neuroimaging at 6 months of age accurately predicted a diagnosis of ASD in 9 out of 11 infants at high familial risk for ASD. These findings demonstrate the potential for early detection of autism in infants at high familial risk and serve as a proof-of-concept that patterns of infant brain measures precede the defining behavioral characteristics of ASD.

Infants with high familial risk begin life with approximately a 20% chance of developing ASD (36) compared to ~1.5% in infants with low or unknown risk (2). Because of the 1 in 68 prevalence of ASD in the population, the clinical application of functional neuroimaging is likely to be most valuable in evaluating infants at high familial risk. Current intervention research that has focused on the first year of life has been limited to studying entire cohorts of high familial risk infants, with little to no ability to assess a specific individual's likelihood of receiving a diagnosis beyond the expected recurrence risk. In our sample, even in the lower bound of the confidence interval, the positive predictive value of this classifier shows a much higher ability to correctly detect ASD risk in 6-month-old infants than is possible with behavioral assessment alone. If these results are replicated in a new high-risk infant cohort, functional neuroimaging at 6 months of age could provide a clinically valuable tool for the detection of ASD in high-risk infants, prior to the development of the full syndrome. This would open the door to randomized controlled trials aimed at identifying effective interventions by recruiting high-risk infants who have been identified as having an even greater risk based on their 6-month neuroimaging assessment.

While we have taken many precautions to test the internal validity of our classification analysis, future research may be necessary before the clinical utility of this method can be fully realized. First, while our results are very strong within this sample of high-risk infants, a general classifier will likely require a much larger sample to demonstrate its ability to capture the full breadth of the heterogeneity in ASD. Even with this limited sample size, the ability of the classifier to predict an individual infant's later diagnosis is substantial. This high accuracy was maintained when the classifier was trained on a smaller sub-sample and used to predict 10 independent infants, suggesting that these results are fairly robust. Second, MRI is likely too expensively to be feasible as a general screening tool. If these findings could be generalized to more cost-effective and mobile neuroimaging technologies, it would greatly increase the accessibility of early screening. Despite these limitations, these results suggest that early differences in the brain's functional connections are useful in predicting a later diagnosis of ASD as early as 6 months of age, well before the onset of the defining behavioral characteristics of ASD.

In conclusion, these results show that functional neuroimaging with six-month-old infants at high familial risk for ASD can accurately predict which individuals receive a clinical diagnosis of ASD at 24 months of age. Ultimately, this study represents an initial, but critical, first step toward developing the earliest diagnostic methods available, and may yield the clues necessary to build efficacious early interventions based on individual risk profiles.

Materials and Methods

Experimental Design

Participants were part of the Infant Brain Imaging Study, an ongoing longitudinal study of infants at low- and high-familial risk for ASD. Infants were recruited, screened, and assessed at one of four clinical sites: University of North Carolina, University of Washington, The Children's Hospital of Philadelphia, and Washington University in St. Louis. The research protocol was approved by the institutional review board at all clinical sites, and parents provided written informed consent after receiving a detailed description of the study. Data were used for research purposes only.

A high-familial-risk-for-ASD (HR) cohort of 59 infants was included in this study: 11 ASD-pos (diagnosed with ASD at 24 months) and 48 ASD-neg (non-ASD at 24 months). High-risk infants were defined as having at least one sibling with an ASD diagnosis. Participants were excluded for comorbid medical or neurological diagnoses influencing growth, development, or cognition; prior genetic conditions; premature birth or low birth weight; maternal substance abuse during pregnancy; contraindication for MRI; or family history of psychosis, schizophrenia, or bipolar disorder.

Diagnostic Testing

All infants included in these analyses participated in a comprehensive battery of behavioral assessments including the Autism Diagnostic Observation Schedule (ADOS) (37) and Autism Diagnostic Interview-Revised (ADI-R) (38) at 24 months. The ADOS and all other testing and interview data were independently reviewed by experienced clinicians for DSM-IV-TR (39) criteria for autistic disorder or pervasive developmental disorder not otherwise specified. All ASD-positive infants were assigned a diagnosis according to clinical best estimate using DSM-IV-TR at 24 months of age.

Cognitive and Behavioral Assessments

The Repetitive Behavior Scale-Revised (RBS-R) (40, 41) is a parent/caregiver rated measure covering a broad range of repetitive behaviors. The RBS-R is a questionnaire that focuses exclusively on restricted/repetitive behaviors. It includes 43 items rated on a four-point scale: 0=behavior does not occur; 1=behavior occurs and is a mild problem; 2=behavior occurs and is a moderate problem; and 3=behavior occurs and is a severe problem. Items are grouped into 6 conceptually derived subscales: Stereotyped Behavior; Self-injurious Behavior; Compulsive Behavior; Ritualistic Behavior; Sameness Behavior; and Restricted Behavior. Scores on these subscales were used to determine brain-behavior features used in the analysis.

The Mullen Scales of Early Learning (MSEL) (42) is a standardized, normed, developmental assessment that provides an overall index of cognitive ability and delay. Children were assessed at 24 months of age and their scores on the Receptive Language, Expressive Language, Visual Reception, Fine Motor, and Gross Motor subscales were used to determine brain-behavior features used in the analysis.

The Communication and Symbolic Behavior Scales-Developmental Profile (CSBS-DP) (43) is designed to elicit social and communicative behaviors in infants and was administered at each participant's 24-month visit. Specifically, their scores on items measuring initiation of joint attention and social interaction were used to determine brain-behavior features in the primary analysis. These items were chosen to reflect specific aspects of behavior that we reasoned to be particularly relevant to social development at approximately 2 years of age.

Image Acquisition

All scans were acquired at IBIS Network clinical sites using cross-site calibrated 3-T Siemens TIM Trio scanners (Siemens Medical Solutions, Malvern, Pa.) equipped with standard 12-channel head coils. Images were acquired during natural infant sleep without sedation. The IBIS imaging protocol included anatomical images (T1- and T2-weighted), diffusion tensor images (25-direction and 65-direction HARDI DWI), and resting state fcMRI. This study used a 3D T2 W sequence (TE=497 ms, TR=3200 ms, matrix 256×256×160, 1 mm3 voxels, sagittal acquisition) and a gradient-echo echo planar image (EPI) functional sequence (TE=27 ms, TR=2500 ms, field of view 256 mm, matrix 64×64, voxel size 4 mm3, flip angle 90°, bandwidth 1906 Hz). All included infants provided data collected during at least two fMRI runs, each run comprising 130 temporally contiguous frames (5.4 minutes).

fMRI Preprocessing

Initial fMRI data preprocessing followed previously described procedures (25, 44, 45) including (i) compensation for slice dependent time shifts using sinc interpolation, (ii) correction of systematic odd-even slice intensity differences caused by interleaved acquisition, and (iii) spatial realignment to compensate for head motion within and across fMRI runs. Atlas registration of the functional data was achieved by a sequence of affine transforms (individual fMRI average volume—individual T2 W—atlas-representative target). All data were registered to an age specific (6-month) target atlas to handle shape differences across developmental age categories (46). The volumetric time series were resampled in atlas space (3 mm3 voxels) using a resampling procedure that applied all affine registration transform and correction for head movement in a single step. Each atlas-transformed functional dataset was visually inspected in sagittal, transverse, and coronal views to exclude potential errors not otherwise identified.

Frame Censoring

Head motion, even of sub-millimeter magnitude, has been identified as a non-physiological source of spurious variance in resting-state fMRI data (47-49). Data were subjected to rigorous frame censoring based on the frame-to-frame displacement (FD) measure 12 which quantifies movement as the sum of the magnitudes of translational movement (X, Y, Z) and rotational movement (Pitch, Yaw, Roll) evaluated at a radius of 50 mm. Frames with FD>0.2 mm were marked for subsequent censoring. Temporally isolated frames, where there were fewer than 6 contiguous frames of FD<0.2 mm, were also censored. Each of the fMRI runs with fewer than 30 uncensored frames was discarded. To control for potential biases attributable to the amount of data per cohort, exactly 150 non-censored frames were used for correlation analysis in each subject, where runs with the largest number of usable frames were prioritized.

fcMRI Preprocessing

In addition to the previously published procedures (50), further preprocessing was conducted prior to computation of region-of-interest (ROI) pair time series correlations. Using only the non-censored frames, the data were voxel-wise demeaned and detrended within runs, and nuisance waveforms were regressed out. Nuisance regressors included (i) the time series of three translation (X, Y, Z) and three rotation (Pitch, Yaw, Roll) estimates derived by retrospective head motion correction and Volterra expansion derivatives to comprise 24 total motion regressors (51), and (ii) time series derived from the regions of non-interest (whole brain, white matter, and cerebrospinal fluid) and their first derivatives. Following nuisance regression, data in frames marked for censoring were replaced by interpolated values computed by least-squares spectral analysis (50, 52). The fMRI data were then temporally filtered to retain frequencies in the 0.009 Hz<f<0.08 Hz band. As a last step, the data were spatially smoothed using a Gaussian kernel (6 mm FWHM isotropic).

Definition of ROIs and Correlation Computation

Candidate regions of interest (ROIs: n=280) were adopted from a combination of meta-analyses of ASD studies (44) and of task data and cortical functional areal parcellations obtained in healthy adults (45). Three viewers inspected ROI placements in age-specific atlas templates. Of the 280 ROIs, 50 were partially outside the whole brain mask and were removed, leaving 230 usable ROIs (25). ROI-representative time series were calculated as the average of the time series of each voxel intersecting the 10 mm diameter sphere located at a given ROI center. Pairwise Pearson correlation values were generated from each of the 26,335 possible pairs of ROIs and then Fisher-z transformed to improve normality.

Identification of Brain-Behavior Features

To define the feature space, a leave-one-out cross-validation analysis was performed to identify a set of functional connections that were both related to behavior and showed differences between groups. We generated 59 sets of features by iteratively removing one subject from the analysis. For each iteration the remaining 58 subjects were used to define region pairs whose connectivity showed both a nominal Pearson correlation with behavior (p<0.05) and difference between groups (t-test, p<0.05). The feature space was then defined as the intersection (100% consensus) of these sets. To demonstrate that these features can discriminate between the infant groups, a principal component analysis was used to define the top two dimensions of variance across all participants. Participants scores on the first and second principal components of this feature space were plotted against each other in FIG. 2.

Predicting Individual 24-Month Clinical Diagnoses

To determine whether or not these features were capable of predicting the clinical diagnostic outcome of an individual infant, the feature selection process described immediately above was repeated as a separate analysis, but with two important differences.

First, a participant was removed from the analysis before feature selection to serve as an independent test case. The remaining participants were used to train a linear support vector machine (SVM) classifier. This strategy was repeated using each participant as the test case, creating a fully cross-validated approach with a "nested" leave-one-out procedure to identify features. As a result, the estimation of accuracy was relatively unbiased in the sense that the training features were selected independently of each test case (53Z).

Second, functional connections between ROI pairs were selected using only information about their correlation with behavior (p<0.05) across the training group without using knowledge of the group labels (diagnostic outcomes). Similar methods are discussed in detail by Pereira et al. (33), with many of the applications reviewed by Gabrieli et al. (29).

For each test case, features were determined within the training set as the functional connections between ROI pairs that show a nominally significant (p<0.05) behavioral correlation within the feature space across all of the nested sets (100% consensus). These features were then used to train a classifier with a linear kernel to discriminate between infants who are and are not diagnosed with ASD at 24 months. Finally, the classifier was used to predict the independent test case.

The significance of the classification accuracy was determined by repeating the analysis using random group labels for each test case to estimate the null distribution of classification accuracy. This procedure was repeated 10,000 times in order to determine how many times a randomly constructed classifier would perform as well as a classifier trained with the correct group labels. This distribution and the observed accuracy of the correct labels is shown in FIG. 3.

Whole-Brain Visualization

To visualize functional connections that likely contribute to the accuracy of this classification approach, each pair of ROIs that were used in each of the nested feature sets (100% consensus) are projected onto a Talairach brain in FIGS. 4A-C. The Talairach coordinates and average connectivity values by group for these regions are listed in table 600 of FIGS. 6A-6B. These calculations are only for visualization and should not be interpreted as differences directly contributing to any individual's classification.

Leave-10-Out

To complete the leave-10-out analysis, the nested cross-validation procedure was repeated with a random set of 10 infants initially removed as the independent test set. To maintain the general population frequency distribution, each set of 10 consisted of 2 randomly selected ASD-pos and 8 randomly selected ASD-neg children. This analysis was run with 1000 random sets, allowing us to assess the distribution of classifier accuracies when more subjects were kept independent. This represents a very small sample of the full set of randomized permutations; however, this analysis is meant to serve only as a demonstration of the robustness of the classification analysis.

Random Features

To test how well random features could classify diagnostic outcomes, the nested cross-validation procedure was repeated and the features of each nested iteration were replaced with a random sample of the same number of features. For example, if a nested feature detection resulted in 400 ROI pairs that were related to the 24-month behaviors, the resulting 400 pairs were replaced with 400 random ROI pairs. When repeated for each test case, the ability of random features to classify clinical outcome represents the chance that the accuracy of our primary analysis is driven solely by the amount of features used in the analysis. We repeated this analysis 1000 times and report the average and standard deviation of the classifier accuracy.

Statistical Analysis

All classification analyses were completed using MATLAB's Statistics and Machine Learning Toolbox (Mathworks Inc., Natick, Mass., USA). Support vector machines were trained using a linear kernel using the default setting of the fitcsvm function, and individual subjects were predicted using the predict function. Scripts were designed in-house, and their workflow is detailed above. Principal components were calculated using the default settings of the pca function to create a linear combination of the features space which was then used for the visualization in FIG. 2.

Individual Classification Accuracy

Since a primary goal is diagnostic classification for individuals, we also measured the individual classification accuracy, following Green et al. (56), to understand how reliably each infant was classified across the nested models. This analysis determines the rate at which each of the 59 individuals is classified accurately by testing an SVM classifier created from each of the nested sets used in the primary analysis. This analysis is akin to a leave-two-out-cross validation method in which one participant (test case) is removed while the remaining participants underwent the LOOCV procedure. Each nested set is trained on a slightly different training set, allowing the test case to be classified with 57 separate models. The test case is then tested on each of those models, and an average individual accuracy was calculated for that case.

Figure 5:
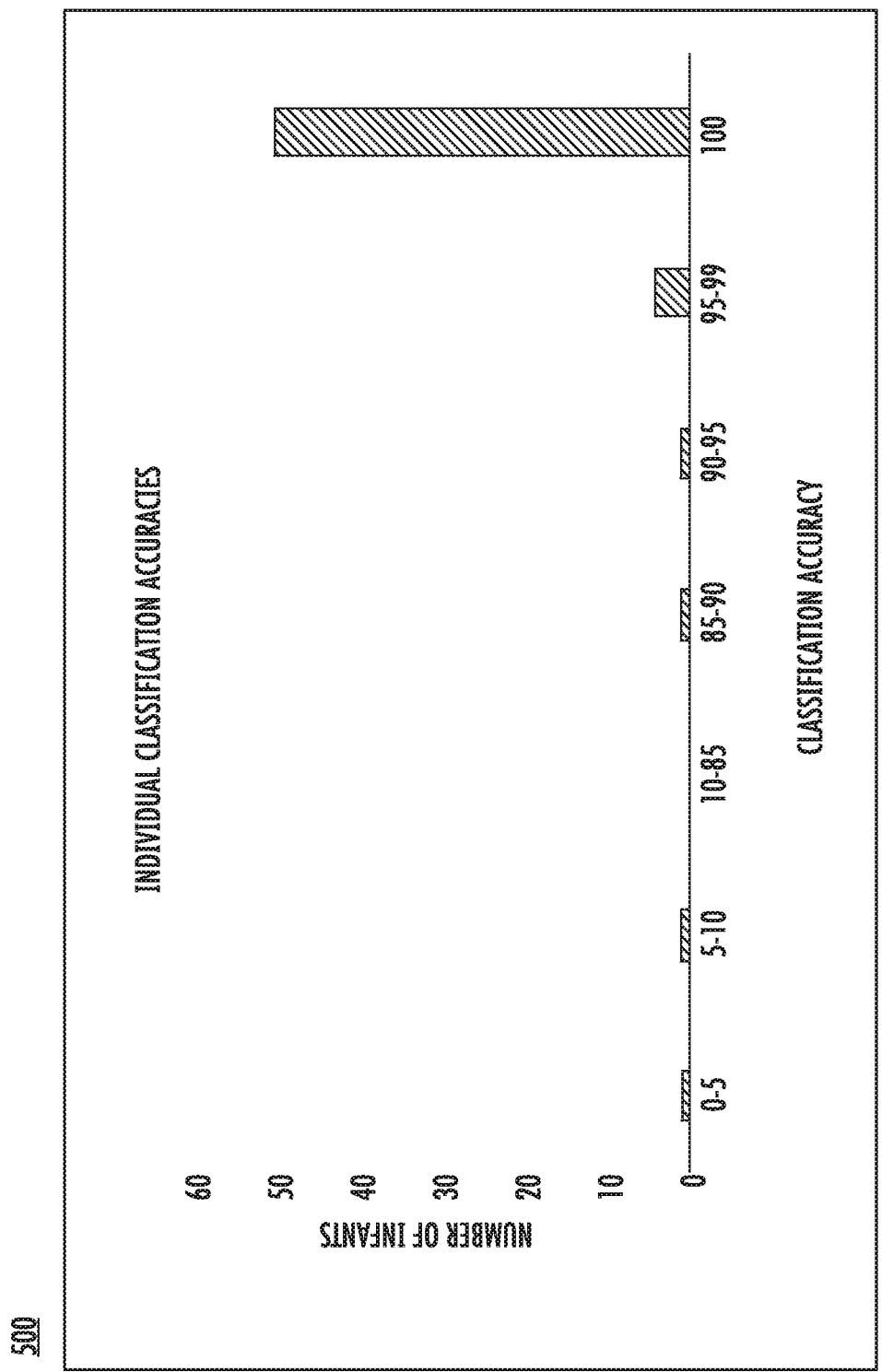
FIG. 5 depicts individual classification accuracies based on an example classification model.

Once repeated using each participant as a test case, individual accuracy can be measured for each individual, reflecting how reliably that participant is classified across models. FIG. 5 is a diagram 500 that depicts these individual classification accuracies.

Comparison to Independent High-Risk Sample

In order to ensure that our sample of high-risk infants was representative of the general population of high-risk individuals, we compared the 24-month behavioral scores from our sample of infants to scores from an independent sample of high-risk infants. The comparison group is made up of 68 participants that were collected as part of the Infant Brain Imaging Study, but were not included in the main analysis because they did not complete a 6-month MRI visit.

This group consisted of 20 ASD-pos and 48 ASD-neg 24-month-old participants. Unpaired t-tests were used to assess between-groups differences on scores from the RBS-R, MSEL, and CSBS. These results are presented in a table 700 of FIG. 7. Overall, these results suggest that there are no apparent differences between the high-risk sample used in our main analysis and this additional independent sample of high-risk infants. This supports the conclusion that our classifier results are likely to generalize to other high-risk infants.

Figure 8:
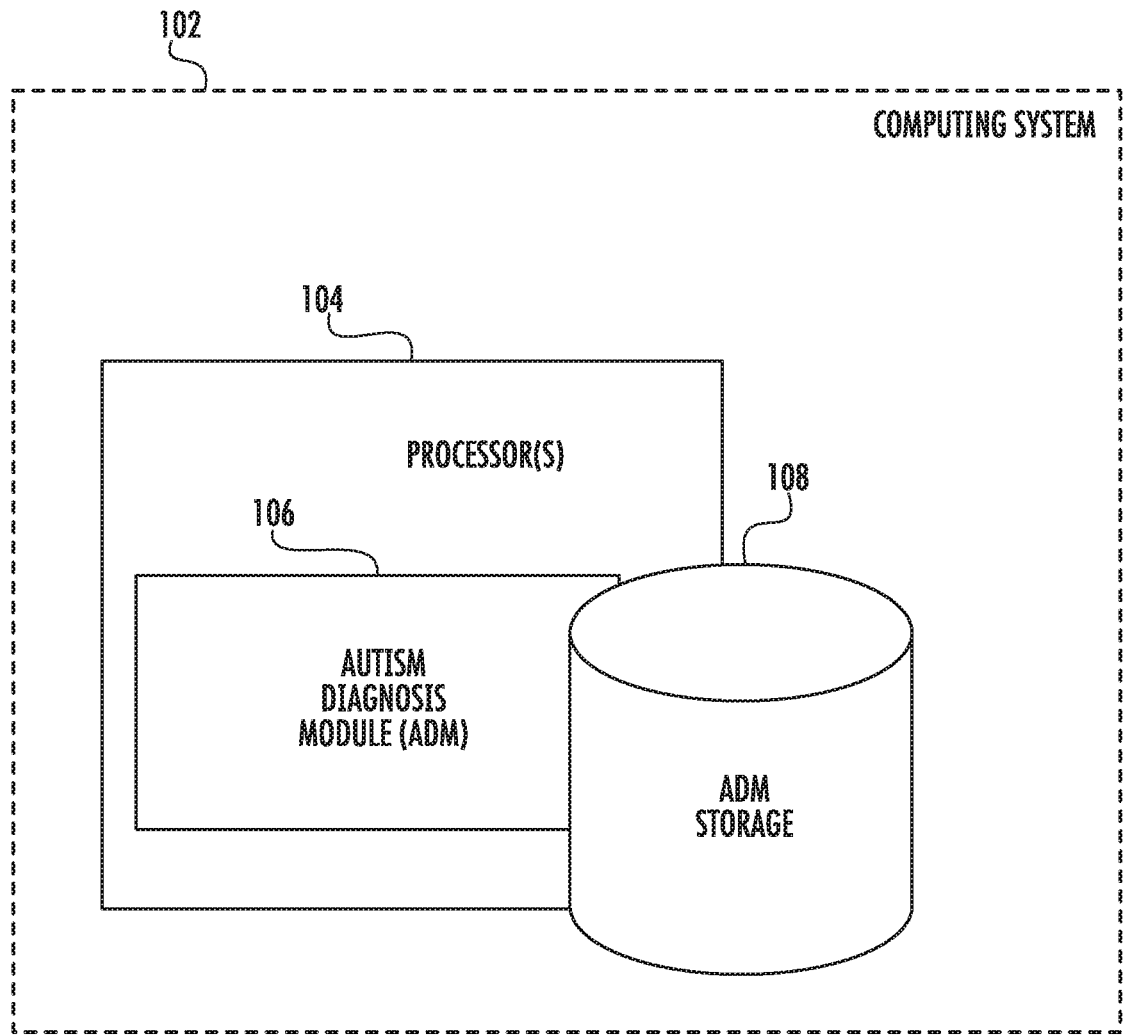
FIG. 8 is a diagram illustrating an example system for utilizing functional connectivity brain imaging for diagnosis of a neurobehavioral disorder according to an embodiment of the subject matter described herein.

FIG. 8 is a diagram illustrating an example system 102 (e.g., a single or multiple processing core computing device) for utilizing functional connectivity brain imaging for diagnosis of a neurobehavioral disorder according to an embodiment of the subject matter described herein. System 102 may be any suitable entity, such as a medical device or one or more computing devices or platforms, for performing one or more aspects of the subject matter described herein, e.g., utilizing functional connectivity brain imaging for diagnosis of a neurobehavioral disorder.

In some embodiments, components, modules, and/or portions of system 102 may be implemented or distributed across multiple devices or computing platforms. For example, system 102 may involve multiple computers configured to perform various functions, such as obtaining magnetic resonance imaging (MRI) or functional connectivity MRI (fcMRI) data, analyzing functional brain imaging data based on certain brain regions of interest associated with one or more autism spectrum disorder (ASD) related behaviors, and/or predicting a neurobehavioral disorder diagnosis or an autism spectrum disorder (ASD) diagnosis using deep learning or neural network techniques.

In some embodiments, system 102 may include one or more processor(s) 104, a neurobehavioral disorder diagnosis module (ADM) 106, and an ADM storage 108. Processor(s) 104 may represent or include a physical processor, a general purpose microprocessor, a single-core processor, a multi-core processor, a field-programmable gate array (FPGA), and/or an application-specific integrated circuit (ASIC). In some embodiments, processor(s) 104 may be configured to execute software stored in one or more non-transitory computer readable media, such as ADM storage 108 in system 102. For example, software may be loaded into a memory structure for execution by processor(s) 104. In some embodiments, e.g., where system 102 includes multiple processors, some processor(s) 104 may be configured to operate independently of other processor(s) 104.

ADM 106 may be any suitable entity or entities (e.g., software executing on processor(s) 104, an ASIC, an FPGA, or a combination of software, an ASIC, or an FPGA) for performing one or more aspects associated with diagnosing autism using functional brain imaging. In some embodiments, ADM 106 may be implemented using processor(s) 104 and/or one or more memories, such as ADM storage 108. For example, ADM 106 may utilize processor(s) 104 (e.g., using software stored in local memory) and random access memory (RAM).

ADM 106 may include functionality for receiving brain imaging data for a subject. For example, ADM 106 may receive brain imaging data from ADM storage 108 or an imaging data storage system. In another example, ADM 106 may include or communicate with an imaging system, such as an MRI scanner, to receive brain imaging data.

In some embodiments, ADM 106 may include or utilize one or more communications interfaces, e.g., one or more network interface cards (NICs), for interacting with various computers and/or other devices. For example, ADM 106 may use one or more communications interfaces for receiving and sending various types of data units; such as Internet protocol (IP) messages, Ethernet frames, Ethernet messages, or packet data units (PDUs). In another example, ADM 106 may utilize application programming interfaces (APIs) and/or graphical user interfaces (GUIs) to receive or obtain imaging data, such as MRI scans, and may use such interfaces to obtain information about a subject and/or to notify an entity (e.g., a medical worker and/or a subject's guardian) about a prediction regarding a neurobehavioral disorder diagnosis.

In some embodiments, ADM 106 may pre-process brain imaging data, such as functional MRI (fMRI) or fcMRI data. For example, ADM 106 may trigger or perform fMRI data preprocessing that includes compensation for slice dependent time shifts using sinc interpolation, correction of systematic odd-even slice intensity differences caused by interleaved acquisition, and/or spatial realignment to compensate for head motion within and across fMRI runs. In this example, atlas registration of the functional data may be achieved by a sequence of affine transforms (individual fMRI average volume—individual T2 W—atlas-representative target) and all data may be registered to an age specific (6-month) target atlas to handle shape differences across developmental age categories (46). The volumetric time series may be resampled in atlas space (3 mm3 voxels) using a resampling procedure that applied all affine registration transform and correction for head movement in a single step.

In some embodiments, ADM 106 may predict, using at least one functional connectivity feature based on fcMRI data associated with a subject and at least one machine learning classification algorithm, a neurobehavioral disorder diagnosis associated with the subject. For example, ADM 106 may identify brain regions of interest (ROIs) based on areas believed to be associated with ASD related behaviors, e.g., social interaction, language, and/or repetitive behaviors. In this example, fMRI and/or fcMRI data may be analyzed for each relevant ROI to obtain a ROI-representative time series calculated as the average of the time series of each voxel intersecting a 10 millimeter diameter sphere located at a given ROI center.

In some embodiments, ADM 106 may utilize brain ROI pairs whose connectivity indicate both a nominal Pearson correlation with behavior (e.g., $p<0.05$) and difference between groups (e.g., t-test, $p<0.05$). For example, ADM 106 or a related entity may identify relevant brain-behavior features by using imaging data (e.g., fcMRI data) to identify a set of functional connections that are both related to behavior and showed differences between groups (e.g., those that have ASD and those that do not have ASD).

In some embodiments, to determine whether or not some connectivity features are capable of predicting the clinical diagnostic outcome of an individual subject, a feature selection process described above may be performed as a separate analysis, but with two important differences. First, a participant was removed from the analysis before feature selection to serve as an independent test case. The remaining participants were used to train a linear support vector machine (SVM) classifier. This strategy was repeated using each participant as the test case, creating a fully cross-validated approach with a "nested" leave-one-out procedure to identify features. As a result, the estimation of accuracy was relatively unbiased in the sense that the training features were selected independently of each test case. Second, functional connections between ROI pairs were selected using only information about their correlation with behavior ($p<0.05$) across the training group without using knowledge of the group labels (e.g., diagnostic outcomes).

In some embodiments, ADM 106 or a related entity may train a deep learning network using various brain imaging data and/or relevant functional connections. For example, ADM 106 may use behavior related features to train a classifier with a linear kernel (e.g., a linear SVM classifier) to discriminate between subjects (e.g., infants) who are and are not diagnosed with ASD at 24 months of age.

ADM storage 108 may be any suitable entity or entities (e.g., one or more memory devices) for storing information associated with diagnosing autism or ASD using functional brain imaging. For example, ADM storage 108 may store one or more machine learning algorithms, MRI data or other medical imaging data, various subject (e.g., patient) information, and/or diagnosis related information. In another example, ADM storage 108 may store information about testing, treatments, or interventions.

It will be appreciated that FIG. 8 is for illustrative purposes and that various nodes, their locations, and/or their functions may be changed, altered, added, or removed. For example, some nodes and/or functions may be combined into a single entity. In a second example, a node and/or function may be located at or implemented by two or more nodes.

Figure 9:
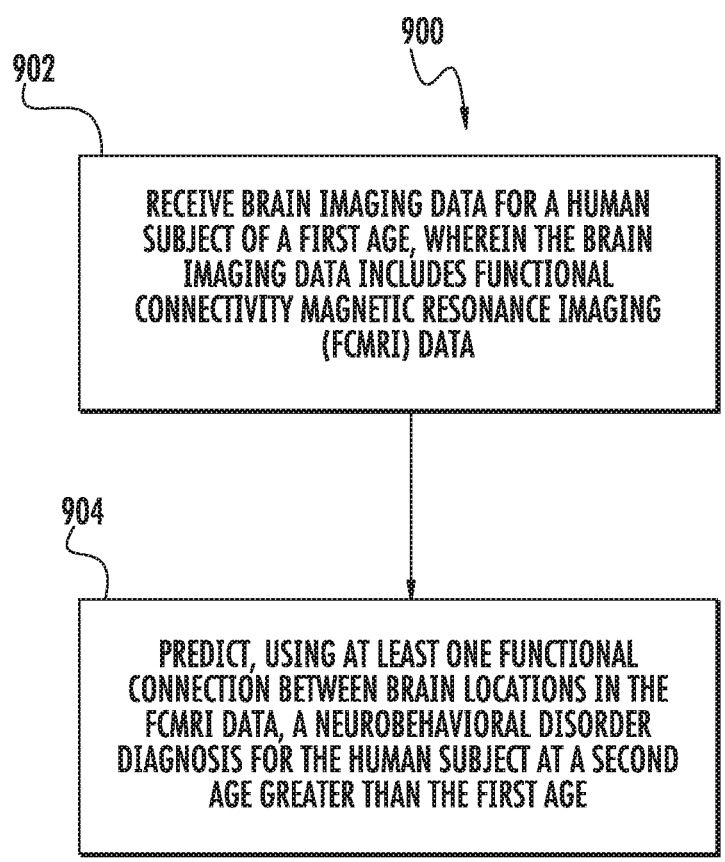
FIG. 9 is a diagram illustrating an example process for utilizing functional connectivity brain imaging for diagnosis of a neurobehavioral disorder according to an embodiment of the subject matter described herein.

FIG. 9 is a diagram illustrating an example process 900 for utilizing functional connectivity brain imaging for diagnosis of a neurobehavioral disorder according to an embodiment of the subject matter described herein. In some embodiments, process 900, or portions thereof, may be performed by or at system 102, a computer communicatively connected to system 102, or another node.

Referring to FIG. 9, in step 902, brain imaging data for a human subject of a first age may be received. For example, brain imaging data may include fcMRI data for a human subject that is presymptomatic and/or is under two years old.

In some embodiments, brain imaging data may be pre-processed by compensating for slice dependent time shifts using sinc interpolation, correction of systematic odd-even slice intensity differences caused by interleaved acquisition, or spatial realignment to compensate for head motion within and across imaging acquisition.

In step 904, a neurobehavioral disorder diagnosis for the human subject at a second age greater than the first age may be predicted using at least one functional connection between brain locations in the fcMRI data.

In some embodiments, a first age may be six months and a second age may be two years or older.

In some embodiments, after predicting a neurobehavioral disorder diagnosis associated with a subject, an intervention action may be performed based on the prediction. For example, an intervention action may include scheduling a subject for further testing, initiating an intervention or treatment, or notifying a medical worker about the diagnosis.

In some embodiments, a neurobehavioral disorder may comprise ASD and at least one functional connection may be located within at least one brain ROI associated with an ASD behavior.

In some embodiments, at least one brain ROI may be related to social behavior, language, motor development, and/or repetitive behavior.

In some embodiments, at least one functional connection used to predict a neurobehavioral disorder diagnosis may be selected using a machine learning algorithm that takes as input behaviorally-related functional connections and known diagnostic outcomes and learns a set of functional connections that predict the neurobehavioral disorder diagnosis.

In some embodiments, at least one machine learning classification algorithm may comprise a trained linear SVM classifier.

In some embodiments, a neurobehavioral disorder may include autism spectrum disorder, a neurological developmental disorder, or a behavioral disorder.

It should be noted that system 102, ADM 106, and/or functionality described herein may constitute a special purpose computing device. Further, system 102, ADM 106, and/or functionality described herein can improve the technological field of early autism detection.

Each of the following references is incorporated herein by reference in its entirety:

REFERENCES

1. Diagnostic and statistical manual of mental disorders, 5th ed. (American Psychiatric Association Arlington, Va., 2013).
2. Developmental, Disabilities Monitoring Network Surveillance Year, and 2010 Principal Investigators, Prevalence of autism spectrum disorder among children aged 8 years-autism and developmental disabilities monitoring network (Morbidity and mortality weekly report, Surveillance summaries, Washington, D C, 2002).
3. M. L. Ganz, The lifetime distribution of the incremental societal costs of autism. Arch Pediatr. Adolesc. Med. 161, 343-9 (2007).
4. A. V. S. Buescher, Z. Cidav, M. Knapp, D. S. Mandell, Costs of Autism Spectrum Disorders in the United Kingdom and the United States. JAMA Ped. 168, 721-8 (2014).
5. S. L. Webb, E. J. H. Jones, J. Kelly, G. Dawson, The motivation for very early intervention for infants at high risk for autism spectrum disorders. Int. J. Speech. Lang. Pathol. 16, 36-42 (2014).
6. S. J. Rogers, L. Vismara, A. L. Wagner, C. McCormick, G. Young, S. Ozonoff, Autism treatment in the first year of life: a pilot study of infant start, a parent-implemented intervention for symptomatic infants. J. Autism. Dev. Disord. 44, 2981-95 (2014).
J. Green, T. Charman, A. Pickles, M. W. Wan, M. Elsabbagh, V. Slonims, C. Taylor, J. McNally, R. Booth, T. Gliga, E. J. Jones, Parent-mediated intervention versus no intervention for infants at high risk of autism: a parallel, single-blind, randomised trial. Lancet. Psyc. 2, 133-40 (2015).

8. S. Ozonoff, A. M. Iosif, F. Baguio, I. C. Cook, M. M. Hill, T. Hutman, S. J. Rogers, A. Rozga, S. Sangha, M. Sigman, M. B. Steinfeld, A prospective study of the emergence of early behavioral signs of autism. J. Am. Acad. Child Adolesc. 49, 256-66 (2010).

9. W. Guthrie, L. B. Swineford, C. Nottke, A. M. Wetherby, Early diagnosis of autism spectrum disorder: stability and change in clinical diagnosis and symptom presentation. J. Child Psychol. Psychiatry. 54, 582-90 (2013).

10. L. Zwaigenbaum, S. Bryson, T. Rogers, W. Roberts, J. Brian, P. Szatmari, Behavioral manifestations of autism in the first year of life. Int. J. Dev. Neurosci. 23, 143-52 (2005).

11. Estes, L. Zwaigenbaum, H. Gu, T. St. John, S. Paterson, J. T. Elison, H. Hazlett, K. Botteron, S. R. Dager, R. T. Schultz, P. Kostopoulos, A. Evans, G. Dawson, J. Eliason, S. Alvarez, J. Piven, Behavioral, cognitive, and adaptive development in infants with autism spectrum disorder in the first 2 years of life. J. Neurodev. Disord. 7, 24 (2015).

12. W. Jones, A. Klin, Attention to eyes is present but in decline in 2-6-month-old infants later diagnosed with autism. Nature. 504, 427-31 (2013).

13. R. L. Landa, A. L. Gross, E. A. Stuart, A. Faherty, Developmental trajectories in children with and without autism spectrum disorders: the first 3 years. Child Dev. 84, 429-42 (2013).

14. J. T. Elison, S. J. Paterson, J. J. Wolff, J. S. Reznick, N. J. Sasson, H. Gu, K. N. Botteron, S. R. Dager, A. M. Estes, A. C. Evans, G. Gerig, H. C. Hazlett, R. T. Schultz, M. Styner, L. Zwaigenbaum, J. Piven, White matter microstructure and atypical visual orienting in 7-month-olds at risk for autism. Am. J. Psychiatry. 170, 899-908 (2013).

15. J. M. Fearnley, A. J. Lees, Ageing and Parkinson's disease: substantia nigra regional selectivity. Brain. 114, 2283-301 (1991).

16. J. J. Wolff, H. Gu, G, Gerig, J, T. Elison, M. Styner, S. Gouttard, K. N. Botteron, S. R. Dager, G. Dawson, A. M. Estes, A. Evans, H. C. Hazlett, P. Kostopoulos, R. C. McKinstry, S. J. Paterson, R. T. Schultz, L. Zwaigenbaum, J. Piven, Differences in white matter fiber tract development present from 6 to 24 months in infants with autism. Am. J. Psychiatry. 169, 589-600 (2012).

17. J. J. Wolff, G. Gerig, J. D. Lewis, T. Soda, M. A. Styner, C. Vachet, K. N. Botteron, J. T. Elison, S. R. Dager, A. M. Estes, H. C. Hazlett, R. T. Schultz, L. Zwaigenbaum, J. Piven, Altered corpus callosum morphology associated with autism over the first 2 years of life. Brain. 138, 2046-58 (2015).

18. M. D. Shen, C. W. Nordahl, G. S. Young, S. L. Wootton-Gorges, A. Lee, S. E. Liston, K. R. Harrington, S. Ozonoff, D. G. Amaral, Early brain enlargement and elevated extra-axial fluid in infants who develop autism spectrum disorder. Brain. 136, 2825-35 (2013).

19. M. Elsabbagh, E. Mercure, K. Hudry, S. Chandler, G. Pasco, T. Charman, A. Pickles, S. Baron-Cohen, P. Bolton, M. H. Johnson, Infant neural sensitivity to dynamic eye gaze is associated with later emerging autism. Curr. Biol. 22, 338-42 (2012).

20. E. S. Finn, X. Shen, D. Scheinost, M. D. Rosenberg, J. Huang, M. M. Chun, X. Papademetris, R. T. Constable, Functional connectome fingerprinting: identifying individuals using patterns of brain connectivity. Nat. Neurosci. 18, 1664-71 (2015).

21. M. D. Rosenberg, E. S. Finn, D. Scheinost, X. Papademetris, X. Shen, R. T. Constable, M. M. Chun, A neuromarker of sustained attention from whole-brain functional connectivity. Nat. Neurosci. 19, 165-71 (2016).

22. R. W. Emerson, J. F. Cantlon, Early math achievement and functional connectivity in the fronto-parietal network. Dev. Cog. Neurosci. 2, S139-51 (2012).

23. Z. Shehzad, A. C. Kelly, P. T. Reiss, D. G. Gee, K. Gotimer, L. Q Uddin, S. H. Lee, D. S. Margulies, A. K. Roy, B. B. Biswal, E. Petkova, The resting brain: unconstrained yet reliable. Cereb. Cortex. 19, 2209-29 (2009).

24. W. Gao, S. Alcauter, J. K. Smith, J. H. Gilmore, W. Lin, Development of human brain cortical network architecture during infancy. Brain Struct. Func. 220, 1173-86 (2014).

25. J. R. Pruett, S. Kandala, S, Hoertel, A. Z. Snyder, J. T. Elison, T. Nishino, E, Feczko, N. U. Dosenbach, B. Nardos, J. D. Power, B. Adeyemo, Accurate age classification of 6 and 12 month-old infants based on resting-state functional connectivity magnetic resonance imaging data. Dev. Cog. Neurosci. 12, 123-33 (2015).

26. N. U. Dosenbach, B. Nardos, A. L. Cohen, D. A. Fair, J. D. Power, J. A. Church, S. M. Nelson, G. S. Wig, A. C. Vogel, C. N. Lessov-Schlaggar, K. A. Barnes, Prediction of individual brain maturity using fMRI. Science. 329, 1358-61 (2010).

27. D. A. Fair, J. T. Nigg, S. Iyer, D. Bathula, K. L. Mills, N. U. Dosenbach, B. L. Schlaggar, M. Mennes, D. Gutman, S. Bangaru, J. K. Buitelaar, Distinct neural signatures detected for ADHD subtypes after controlling for micro-movements in resting state functional connectivity MRI data. Front. Sys. Neurosci. 6,80 (2013).

28. D. J. Greene, J. A. Church, N. U. Dosenbach, A. N. Nielsen, B. Adeyemo, B. Nardos, S. E. Petersen, K. J. Black, B. L. Schlaggar, Multivariate pattern classification of pediatric Tourette syndrome using functional connectivity MRI. Dev. Sci. 1, 1-18 (2016).

29. J. D. Gabrieli, S. S. Ghosh, S. Whitfield-Gabrieli, Prediction as a humanitarian and pragmatic contribution from human cognitive neuroscience. Neuron. 85, 11-26 (2015).

30. F. X. Castellanos, A. Di Martino, R. C. Craddock, A. D. Mehta, M. P. Milham, Clinical applications of the functional connectome. Neuroimage. 80, 527-40 (2013).

31. L. Q. Uddin, K. Supekar, C. J. Lynch, A. Khouzam, J. Phillips, C. Feinstein, S. Ryali, V. Menon, Salience network-based classification and prediction of symptom severity in children with autism. JAMA Psychiatry. 70, 869-79 (2013).

32. C. Ecker, W. Spooren, D. G. M. Murphy, Translational approaches to the biology of Autism: false dawn or a new era & quest. Mol. Psychiatry. 18, 435-42 (2013).

33. F. Pereira, T. Mitchell, M. Botvinick, Machine learning classifiers and fMRI: a tutorial overview. Neuroimage. 45, S199-209 (2009).

34. N. Marrus, H. Underwood-Riordan, F. Randall, Y. Zhang, J. N. Constantino, Lack of effect of risperidone on core autistic symptoms: data from a longitudinal study. J. Child. Adolesc. Psychopharmacol. 24, 513-18 (2014).

35. G. Dawson, S. Rogers, J. Munson, M. Smith, J. Winter, J. Greenson, A. Donaldson, J. Varley, Randomized, controlled trial of an intervention for toddlers with autism: the Early Start Denver Model. Pediatrics. 125, e17-23 (2010).

36. S. Ozonoff, G. S. Young, A. Carter, D. Messinger, N. Yirmiya, L. Zwaigenbaum, S. Bryson, L. J. Carver, J. N. Constantino, K. Dobkins, T. Hutman, Recurrence risk for autism spectrum disorders: a baby siblings research consortium study. Pediatrics. 128, e488-95 (2011).

37. C. Lord, S. Risi, L. Lambrecht, E. H. Cook, B. L. Leventhal, P. C. DiLavore, A. Pickles, M. Rutter, The Autism Diagnostic Observation Schedule-Generic: A 37. standard measure of social and communication deficits associated with the spectrum of autism. J. Autism Dev. Disord. 30, 205-23 (2000).
38. C. Lord, M. Rutter, A. Le Couteur, Autism Diagnostic Interview-Revised: a revised version of a diagnostic interview for caregivers of individuals with possible pervasive developmental disorders. J. Autism Dev. Disord. 24, 659-85 (1994).
39. Diagnostic and statistical manual of mental disorders, 4th ed (American Psychiatric Association, Arlington, Va., 2000).
40. J. W. Bodfish, F. J. Symons, D. E. Parker, M. H. Lewis, Varieties of repetitive behavior in autism: comparisons to mental retardation. J. Autism Dev. Disord. 30, 237-43 (2000).
41. P. Mirenda, I. M. Smith, T. Vaillancourt, S. Georgiades, E. Duku, P. Szatmari, S. Bryson, E. Fombonne, W. Roberts, J. Volden, C. Waddell, Validating the repetitive behavior scale-revised in young children with autism spectrum disorder. J. Autism Dev. Disord. 40, 1521-30 (2010).
42. E. M. Mullen, Mullen Scales of Early Learning: AGS edition (American Guidance Service Publishing, Circle Pines, M N, 1995).
43. A. M. Wetherby, L. Allen, J. Cleary, K. Kublin, H. Goldstein, Validity and reliability of the communication and symbolic behavior scales developmental profile with very young children. J. Speech Lang. Hear. Res. 45, 1202-18 (2002).
44. R. C. Philip, M. R. Dauvermann, H. C. Whalley, K. Baynham, S. M. Lawrie, A. C. Stanfield, A systematic review and meta-analysis of the fMRI investigation of autism spectrum disorders. Neurosci. Biobehav. Rev. 36, 901-42 (2012).
45. J. D. Power, A. L. Cohen, S. M. Nelson, G. S. Wig, K. A. Barnes, J. A. Church, A. C. Vogel, T. O. Laumann, F. M. Miezin, B. L. Schlaggar, S. E. Petersen, Functional network organization of the human brain. Neuron. 72, 665-78 (2011).
46. V. Fonov, A. C. Evans, K. Botteron, C. R. Almli, R. C. McKinstry, D. L. Collins, Unbiased average age-appropriate atlases for pediatric studies. NeuroImage. 54, 313-27 (2011).
47. J. D. Power, K. A. Barnes, A. Z. Snyder, B. L. Schlaggar, S. E. Petersen, Spurious but systematic correlations in functional connectivity MRI networks arise from subject motion. Neuroimage. 59, 2142-54 (2012).
48. T. D. Satterthwaite, D. H. Wolf, K. Ruparel, G. Erus, M. A. Elliott, S. B. Eickhoff, E. D. Gennatas, C. Jackson, K. Prabhakaran, A. Smith, H. Hakonarson, Heterogeneous impact of motion on fundamental patterns of developmental changes in functional connectivity during youth. Neuroimage. 83, 45-57 (2013).
49. K. R. Van Dijk, M. R. Sabuncu, R. L. Buckner, The influence of head motion on intrinsic functional connectivity MRI. Neuroimage. 59, 431-8 (2012).
50. J. D. Power, A. Mitra, T. O. Laumann, A. Z. Snyder, B. L. Schlaggar, S. E. Petersen, Methods to detect, characterize, and remove motion artifact in resting state fMRI. Neuroimage. 84, 320-41 (2014).
51. K. J. Friston, S. Williams, R. Howard, R. S. Frackowiak, R. Turner, Movement-related effects in fMRI time-series. Magn. Reson. Med. 35, 346-55 (1996).
52. Mathias, F. Grond, R. Guardans, D. Seese, M. Canela, H. H. Diebner, G. Baiocchi, Algorithms for spectral analysis of irregularly sampled time series. J Stat Software 11, 1-30 (2004).
53. T. Hastie, R. Tibshirani, J. Friedman, The Elements of Statistical Learning: Data Mining, Inference and Prediction (Springer, New York, 2nd Ed, 2009).
54. D. J. Greene, J. A. Church, N. U. Dosenbach, A. N. Nielsen, B. Adeyemo, B. Nardos, S. E. Petersen, K. J. Black, B. L. Schlaggar, Multivariate pattern classification of pediatric Tourette syndrome using functional connectivity MRI. Dev. Sci. 1, 1-18 (2016).

Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims. It is understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for utilizing functional connectivity brain imaging for predicting a neurobehavioral disorder diagnosis, the method comprising:
   receiving brain imaging data for a human subject of a first age, wherein the brain imaging data includes functional connectivity magnetic resonance imaging (fcMRI) data, wherein the first age is under two years, wherein the first age comprises an age at which the human subject is presymptomatic with respect to a neurobehavioral disorder, wherein the neurobehavioral disorder comprises autism spectrum disorder (ASD);
   determining, using a trained machine learning classification algorithm and a plurality of functional connections between brain locations in the fcMRI data associated with the first age, a neurobehavioral disorder diagnosis of ASD-positive for the human subject prior to a clinical diagnosis of the human subject as ASD-positive at a second age greater than the first age, wherein the second age is two years or older, wherein training the machine learning classification algorithm includes learning the plurality of functional connections used to determine the neurobehavioral disorder diagnosis using behaviorally-related functional connections and known diagnostic outcomes associated with a training data set, wherein each of the behaviorally-related functional connections has a nominally significant behavioral correlation with ASD-related behaviors of human subjects in the training data set assessed at 24 months of age and wherein each of the behaviorally-related functional connections is selected from functional connections within a feature space without using knowledge of the known diagnostic outcomes, wherein the nominally significant behavioral correlation is indicated by a p-value of less than 0.05; and
   performing an intervention action based on the neurobehavioral disorder diagnosis.

2. The method of claim 1 wherein the first age is six months.

3. The method of claim 2 wherein the brain imaging data is preprocessed by performing compensation for slice dependent time shifts using sinc interpolation, correction of systematic odd-even slice intensity differences caused by interleaved acquisition, or spatial realignment to compensate for head motion within and across imaging acquisition.

4. The method of claim 1 wherein at least one functional connection of the plurality of functional connections is located within at least one brain region of interest (ROI) associated with an ASD behavior.

5. The method of claim 4 wherein the at least one brain ROI is related to social behavior, language, motor development, or repetitive behavior.

6. The method of claim 1 wherein the machine learning classification algorithm comprises a trained linear support vector machine (SVM) classifier.

7. A system for utilizing functional connectivity brain imaging for predicting a neurobehavioral disorder diagnosis, the system comprising:
at least one processor; and
a neurobehavioral disorder diagnosis module (ADM) implemented using the at least one processor, wherein the ADM is configured for receiving brain imaging data for a human subject of a first age, wherein the first age is under two years, wherein the first age comprises an age at which the human subject is presymptomatic with respect to a neurobehavioral disorder, wherein the neurobehavioral disorder comprises autism spectrum disorder (ASD), wherein the brain imaging data includes functional connectivity magnetic resonance imaging (fcMRI) data; for determining, using a trained machine learning classification algorithm and a plurality of functional connections between brain locations in the fcMRI data associated with the first age, a neurobehavioral disorder diagnosis of ASD-positive for the human subject prior to a clinical diagnosis of the human subject as ASD-positive at a second age greater than the first age, wherein the second age is two years or older, wherein training the machine learning classification algorithm includes learning the plurality of functional connections used to determine the neurobehavioral disorder diagnosis using behaviorally-related functional connections and known diagnostic outcomes associated with a training data set, wherein each of the behaviorally-related functional connections has a nominally significant behavioral correlation with ASD-related behaviors of human subjects in the training data set assessed at 24 months of age and wherein each of the behaviorally-related functional connections is selected from functional connections within a feature space without using knowledge of the known diagnostic outcomes, wherein the nominally significant behavioral correlation is indicated by a p-value of less than 0.05; and for performing an intervention action based on the neurobehavioral disorder diagnosis.

8. The system of claim 7 wherein the first age is six months.

9. The system of claim 8 wherein the brain imaging data is preprocessed by performing compensation for slice dependent time shifts using sinc interpolation, correction of systematic odd-even slice intensity differences caused by interleaved acquisition, or spatial realignment to compensate for head motion within and across imaging acquisition.

10. The system of claim 7 wherein at least one functional connection of the plurality of functional connections is located within at least one brain region of interest (ROI) associated with an ASD behavior.

11. The system of claim 10 wherein the at least one brain ROI is related to social behavior, language, motor development, or repetitive behavior.

12. The system of claim 7 wherein the machine learning classification algorithm comprises a trained linear support vector machine (SVM) classifier.

13. A non-transitory computer readable medium having stored thereon executable instructions that when executed by at least one processor of a computer cause the computer to perform steps comprising:
receiving brain imaging data for a human subject of a first age, wherein the brain imaging data includes functional connectivity magnetic resonance imaging (fcMRI) data, wherein the first age is under two years, wherein the first age comprises an age at which the human subject is presymptomatic with respect to a neurobehavioral disorder, wherein the neurobehavioral disorder comprises autism spectrum disorder (ASD);
determining, using a trained machine learning classification algorithm and a plurality of functional connections between brain locations in the fcMRI data associated with the first age, a neurobehavioral disorder diagnosis of ASD-positive for the human subject prior to a clinical diagnosis of the human subject as ASD-positive at a second age age greater than the first age, wherein the second age is two years or older, wherein training the machine learning classification algorithm includes learning the plurality of functional connections used to determine the neurobehavioral disorder diagnosis using behaviorally-related functional connections and known diagnostic outcomes associated with a training data set, wherein each of the behaviorally-related functional connections has a nominally significant behavioral correlation with ASD-related behaviors of human subjects in the training data set assessed at 24 months of age and wherein each of the behaviorally-related functional connections is selected from functional connections within a feature space without using knowledge of the known diagnostic outcomes, wherein the nominally significant behavioral correlation is indicated by a p-value of less than 0.05; and
performing an intervention action based on the neurobehavioral disorder diagnosis.

* * * * *